(12) United States Patent
Chan et al.

(10) Patent No.: US 6,506,554 B1
(45) Date of Patent: Jan. 14, 2003

(54) CORE STRUCTURE OF GP41 FROM THE HIV ENVELOPE GLYCOPROTEIN

(75) Inventors: David C. Chan, Brookline; Deborah Fass, Cambridge, both of MA (US); Min Lu, New York, NY (US); James M. Berger, Cambridge; Peter S. Kim, Lexington, both of MA (US)

(73) Assignee: Whitehead Institute for Biomedical Research, Cambridge, MA (US)

( * ) Notice: Subject to any disclaimer, the term of this patent is extended or adjusted under 35 U.S.C. 154(b) by 0 days.

(21) Appl. No.: 09/484,925

(22) Filed: Jan. 18, 2000

Related U.S. Application Data

(62) Division of application No. 09/062,241, filed on Apr. 17, 1998, now Pat. No. 6,150,088.
(60) Provisional application No. 60/043,280, filed on Apr. 17, 1997.

(51) Int. Cl.[7] .................................................. C12Q 1/70
(52) U.S. Cl. ......................... 435/5; 435/236; 530/350; 436/501; 436/86
(58) Field of Search .................... 435/5, 974, 236; 436/501, 86; 530/300

(56) References Cited

U.S. PATENT DOCUMENTS

| | | | |
|---|---|---|---|
| 5,444,044 A | 8/1995 | Jiang et al. | 514/12 |
| 5,464,933 A | 11/1995 | Bolognesi et al. | 530/324 |
| 5,656,480 A | 8/1997 | Wild et al. | 435/325 |
| 5,840,843 A | 11/1998 | Jiang et al. | 530/350 |
| 6,150,088 A | 11/2000 | Chan et al. | 435/5 |

FOREIGN PATENT DOCUMENTS

| | | |
|---|---|---|
| WO | WO 94/02505 | 2/1994 |
| WO | WO 96/40191 | 12/1996 |
| WO | WO 98/32848 | 7/1998 |
| WO | WO 00/06599 | 2/2000 |
| WO | WO 00/40616 | 7/2000 |
| WO | WO 01/03723 A1 | 1/2001 |
| WO | WO 01/44286 A2 | 6/2001 |

OTHER PUBLICATIONS

Ferrer, Marc et al., "Selection of gp41–mediated HIV–1 cell entry inhibitors from biased combinatorial libraries of non–natural binding elements," *Nature Structural Biology* 6(10):953–960 (1999).

Blacklow, Stephen C., et al., "A Trimeric Subdomain of the Simian Immunodeficiency Virus Envelope Glycoprotein," *Biochemistry*, 34(46):14955–14962 (1995).

Lu, Min, et al., "A Trimeric Structural Domain of the HIV–1 transmembrane glycoprotein," *Nature Structural Biology*, 2(12):1–8 (1995 Dec.).

Fass, Deborah and Kim, Peter S., "Dissection of a Retrovirus Envelope Protein Reveals Structural Similarity to Influenza Hemagglutinin," *Current Biology*, 5(12):1–7 (Nov. 13, 1995).

Ring, Christine S., et al., "Structure–based Inhibitor Design by Using Protein Models for the Development of Antiparasitic Agents," *Proc. Natl. Acad. Sci. USA*, 90:3583–3587 (1993 Apr.).

Li, Zhe, et al., "Anti–malarial Drug Development Using Models of Enzyme Structure," *Chemistry & Biology*, 1:31–37 (1994 Sept.).

(List continued on next page.)

*Primary Examiner*—Mary E. Mosher
*Assistant Examiner*—Myron G. Hill
(74) *Attorney, Agent, or Firm*—Hamilton, Brook, Smith & Reynolds, P.C.

(57) ABSTRACT

Described are the crystal structure of the α-helical domain of the gp41 component of HIV-1 envelope glycoprotein which represents the core of fusion-active gp41, methods of identifying and designing drugs which inhibit gp41 function and drugs which do so.

6 Claims, 21 Drawing Sheets

(4 of 21 Drawing Sheet(s) Filed in Color)

OTHER PUBLICATIONS

Meng, Elaine C., et al., "Automated Docking with Grid–Based Energy Evaluation," *Journal of Computational Chemistry*, 13(4):505–524 (1992).

Kuntz, Irwin D., "Structure–Based Strategies for Drug Design and Discovery," *Science* 257:1078–1082 (1992 Aug.).

Gallaher, William R., et al., "A General Model for the Transmembrane Proteins of HIV and Other Retroviruses," *Aids Research and Human Retroviruses*, 5(4):431–440 (1989).

Chambers, Philip, et al., "Heptad Repeat Sequences are Located Adjacent to Hydrophobic Regions in Several Types of Virus Fusion Glycoproteins," *Journal of General Virology*, 71:3075–3080 (1990).

Baum, Rudy, "Virus–cell Fusion Targeted for Drug Development," *C&EN* (May 13, 1996).

Delwart, Eric L., et al., "Retroviral Envelope Glycoproteins Contain a 'Leucine Zipper'–like Repeat," *AIDS Research and Human Retroviruses*, (vol. 6(6):703–706 (1990).

Blake, James and Li, Choh Hao, "Adrenocorticotropin. 47. Synthesis and Biological Activity of Adrenocorticotropic Peptides Modified at the Tryptophan Position," *J. Medicinal Chem.* 18(4):423–426 (1975).

Borchardt, Allen et al., "Small Molecule–dependent genetic selection in stochastic nanodroplets as a means of detecting protein–ligand interactions on a large scale," *Chem. & Biol.* 4(12):961–968 (1997).

Bullough, Per A. et al., "Structured of influenza haemagglutinin at the pH of membrane fusion," *Nature* 371:37–43 (1994).

Caffrey, Michael et al., "Three–dimensional solution structure of the 44kDa ectodomain of SIV gp41," *EMBO J.* 17(16):4572–4584 (1998).

Cao, Jie et al., "Effects of Amino Acid Changes in the Extracellular Domain of the Human Immunodeficiency Virus Type 1 gp41 Envelope Glycoprotein," *J. Virology* 67(5):2747–2755 (1993).

Chabala, John C., "Solid–phase combinatorial chemistry and novel tagging methods for identifying leads," *Curr. Opin. Biotech.* 6:632–639 (1995).

Chakrabartty, Avijit et al., "Aromatic Side–Chain Contribution to Far–Ultraviolet Circular Dichroism of Helical Peptides and its Effect on Measurement of Helix Propensities," *Biochemistry* 32:5560–5565 (1993).

Chan, David C., et al., "Evidence that a Prominent Cavity in the Coiled Coil of HIV Type I gp41 is an Attractive Drug Target," *Proc. Natl. Acad. Sci. USA* 95:15613–15617 (1998).

Chan, David C., et al., "Core Structure of gp41 from the HIV Envelope Glycoprotein," *Cell* 89:263–273 (1997).

Chan, David C. and Kim, P.S., "HIV Entry and Its Inhibition," *Cell* 93:681–684 (1998).

Chen, Yee–Hsiung et al., "Determination of the Helix and β Form of Proteins in Aqueous Solution by Circular Dichroism," *Biochemistry* 13(16):3350–3359.

Chen, Benjamin K. et al., "Distinct Modes of Human Immunodeficiency Virus Type 1 Proviral Latency Revealed by Superinfection of Nonproductively Infected Cell Lines with Recombinant Luciferase–Encoding Viruses," *J. Virology* 68(2):654–660 (1994).

Chen, Charlie L. et al., "One Bead–One Compound Combinatorial Peptide Library: Different Types of Screening," *Methods in Enzymology* 267:211–219 (1996).

Chen, Chin–Ho et al., "A Molecular Clasp in the Human Immunodeficiency Virus (HIV) Type 1 TM Protein Determines the Anti–HIV Activity of gp41 Derivatives:Implication for Viral Fusion," *J. Virology* 69(6):3771–3777 (1995).

Cole, James L. and Garsky, Victor M., "Thermodynamics of Peptide Inhibitor Binding to HIV–1 gp41," *Biochemistry* 40:5633–5641 (2001).

Doering Don S. and Matsudaira, Paul, "Cysteine Scanning Mutagenesis at 40 of 76 Positions in Villin Headpiece Maps the F–Actin Binding Site and Structural Features of the Domain," *Biochemistry* 35:12677–12685 (1996).

Dutch, Rebecca Ellis et al., "Paramyxovirus Fusion Protein: Characterization of the Core Trimer, a Rod–Shaped Complex with Helices in Anti–Parallel Orientation," *Virology* 254:147–159 (1999).

Eckert, Debra M., et al., "Inhibiting HIV–1 Entry: Discovery of D–Peptide Inhibitors that Target the gp41 Coiled–Coil Pocket," *Cell* 99:103–115 (1999).

Eckert, Debra M. et al., "Crystal Structure of GCN4–pl$_Q$1, a Trimeric Coiled Coil with Buried Polar Residues," *J. Mol. Biol.* 284:859–865 (1998).

Eckhart, Leopold et al., "Immunogenic Presentation of a Conserved gp41 Epitope of Human Immunodeficiency Virus Type I on Recombinant Surface Antigen of Hepatitis B Virus," *J. Gen. Virol.* 77:2001–2008 (1996).

Edelhoch, Harold, "Spectroscopic Determination of Tryptophan and Tyrosine in Proteins," *Biochemistry* 6:(7):1948–1954 (1967).

Fass, Deborah et al., "Retrovirus envelop domain at 1.7 Å resolution," *Nature Structural Biology* 3(5):465–469 (1996).

Fass, Deborah and Kim, Peter S., "Dissection of a retrovirus envelope protein reveals structural similarity to influenza hemagglutinin," *Current Biology* 5(12):1–7 (1995).

Furuta et al., "Capture of an early fusion–active conformation of HIV–1 gp41," *Nature Structural Biology* 5(4):276–279 (1998).

Harbury, Pehr B. et al., "Repacking protein cores with backbone freedom:Structure prediction for coiled coils," *Proc. Natl. Acad. Sci, USA* 92:8408–8412 (1995).

Harbury, Pehr B. et al., "Crystal structure of an isoleucine–zipper trimer," *Nature* 371:80–83 (1994).

Hirsch, Vanessa M. and Johnson, Philip R., "Pathogenic diversity of simian immunodeficiency viruses," *Virus Research* 32:183–206 (1994).

Hooft, Rob W.W. and Vriend, Gert, "Errors in protein structures," *Nature* 381:272 (1996).

Jiang, Shibo et al., "A conformation–Specific Monoclonal Antibody Reacting with Fusion–Active gp41 from the Human Immunodeficiency Virus Type 1 Envelope Glycoprotein," *J. of Virology* 72(12):10213–10217 (1998).

Jiang, S. et al., "A screening assay for antiviral compounds targeted to the HIV–1 gp41 core structure using a conformation–specific monoclonal antibody," *J. Virol. Methods* 80:85–96 (1999).

Jiang, Shibo et al., "HIV–1 inhibition by a peptide," *Nature* 365:113 (1993).

Jones, T.A. et al., "Improved Methods for Building Protein Models in Electron Density Maps and the Location of Errors in these Models," *Acta Cryst.* A47:110–119 (1991).

Judice, J. Kevin et al., "Inhibition of HIV type 1 infectivity by constrained α–helical peptides:Implications for the viral fusion mechanism," *Proc. Natl. Acad. Sci. USA* 94:13426–13430 (1997).

Kilby, J. Michael et al., "Potent supression of HIV–1 replication in humans by T–20, a peptide inhibitor of gp41–mediated virus entry," *Nature Medicine* 4(11):1302–1307 (1998).

Kliger, Yossef et al., "Mode of Action of an Antiviral Peptide from HIV–1," *J. Biol. Chem.* 276(2):1391–1397 (2001).

Kozarsky, Karen et al., "Glycosylation and Processing of the Human Immunodeficiency Virus Type 1 Envelope Protein," *J. Acquired Immune Deficiency Syndromes* 2:163–169 (1989).

Kubinyi, Hugo, "Combinatorial and computational approaches in structure–based drug design," *Curr. Op. In Drug Disc. & Dev.* 1(1):16–22 (1998).

LaCasse, Rachel A. et al., "Fusion–Competent Vaccines: Broad Neutralization of Primary Isolates of HIV," *Science* 283:357–362 (1999).

Lam, Kit S. et al., "A new type of synthetic peptide library for identifying ligand–binding activity," *Nature* 354:82–84 (1991).

Lambert, D.M. et al., "Peptides from conserved regions of paramyxovirus fusion (F) proteins are potent inhibitors of viral fusion," *Proc. Natl. Acad. Sci. USA* 93:2186–2191 (1996).

Letvin, Norman L., "Progress in the Development of an HIV–1 Vaccine," *Science* 280:1875–1880 (1998).

Lu, Min and Kim, Peter S., "A Trimeric Structural Subdomain of the HIV–1 Transmembrane Glycoprotein," *J. Biomol. Structure & Dynamics* 15(3):465–471 (1997).

Malashkevich, Vladimir N. et al., "Crystal structure of the simian immunodeficiency virus (SIV) gp41 core: Conserved helical inteactions underlie the broad inhibitory activity of gp41 peptides," *Proc. Natl. Acad. Sci. USA* 95:9134–9139 (1998).

Malashkevich, Vladimir N. et al., "Core structure of the envelope glycoprotein GP2 from Ebola virus at 1.9–Å resolution," *Proc. Natl. Acad. Sci. USA* 96:2662–2667 (1999).

Muster, Thomas et al., "Cross–Neutralizing Activity against Divergent Human Immunodeficiency Virus Type 1 Isolates Induced by the gp41 Sequence ELDKWAS," *J. Virology* 68(6):4031–4034 (1994).

Muster, Thomas et al., "A Conserved Neutralizing Epitope of gp41 of Human Immunodeficiency Virus Type 1," *J. Virology* 67(11):6642–6647 (1993).

Nautiyal, Shivani and Alber, Tom, "Crystal structure of a designed, thermostable, heterotrimeric coiled coil," *Protein Science* 8:84–90 (1999).

Nolte, Alexis et al., "Mirror–design of L–oligonucleotide ligands binding to L–arginine," *Nature Biotechnology* 4:1116–1119 (1996).

O'Neil, Karyn T. and DeGrado, William F., "A Thermodynamic Scale for the Helix–Forming Tendencies of the Commonly Occurring Amino Acids," *Science* 250:646–351 (1990).

Purtscher, Martin et al., "Restricted antigenic variability of the epitope recognized by the neutralizing gp41 antibody 2F5," *AIDS* 10:587–593 (1996).

Reimann, Keith A. et al., "A Chimeric Simian/Human Immunodeficiency Virus Expressing a Primary Patient Human Immunodeficiency Virus Type 1 Isolate env Causes an AIDS–Like Disease after In Vivo Passage in Rhesus Monkeys," *J. Virology* 70(10):6922–6928 (1996).

Richman, Douglas D., "Nailing down another HIV target," *Nature Medicine* 4(11):1232–1233 (1998).

Rimsky, Laurence T. et al., "Determinants of Human Immunodeficiency Virus Type 1 Resistance to gp41–Derived Inhibitory Peptides," *J. Virology* 72(2):986–993 (1998).

Root, Michael J. et al., "Protein Design of an HIV–1 Entry Inhibitor," *Science* 291:884–888 (2001).

Schumacher, Ton N.M. et al., "Identification of D–Peptide Ligands Through Mirror–Image Phage Display," *Science* 271:1854–1857 (1996).

Shuker, Suzanne B. et al., "Discovering High–Affinity Ligands for Proteins: SAR by NMR," *Science* 274:1531–1534 (1996).

Singh, Mona et al. "LearnCoil–VMF: Computational Evidence for Coiled–coil–like Motifs in Many Viral Membrane––fusion Proteins," *J. Mol. Biol.* 290:1031–1041 (1999).

Tan, Kemin et al., "Atomic structure of a thermostable subdomain of HIV–1 gp41," *Proc. Natl. Acad. Sci. USA* 94:12303–12308 (1997).

Tarrago–Litvak, Laura et al., "The reverse transcriptase of HIV–1: from enzymology to therapeutic intervention," *FASEB J.* 8:497–503 (1994).

Tucker, Thomas J. et al., "Development of Nonnucleoside HIV Reverse Transcriptase Inhibitors," *Methods in Enzymology* 275:440–472 (1996).

Tyagi, Sanjay et al., "Multiocolor molecular beacons for allele discrimination," Nature Biotechnology 16:49–53 (1998).

Weissenhorn, Winfried et al., "Assembly of a rod–shaped chimera of a trimeric GCN4 zipper and the HIV–1 gp41 ectodomain expressed in *Escherichia coli,*" *Proc. Natl. Acad. Sci. USA* 94:6065–6069 (1997).

Weissenhorn, W. et al., "Atomic structure of the ectodomain from HIV–1 gp41," *Nature* 387:426–430 (1997).

Weissenhorn, Winfried et al., "Crystal Structure of the Ebola Virus Membrane Fusion Subunit, GP2, from the Envelope Glycoprotein Ectodomain," *Molecular Cell* 2:605–616 (1998).

Wild, Carl et al., "A synthetic peptide inhibitor of human immunodeficiency virus replication: Correlation between solution structure and viral inhibition," *Proc. Natl. Acad. Sci. USA* 89:10537–10541 (1992).

Wild, Carl T. et al., "Peptides corresponding to a predictive α–helical domain of human immunodeficiency virus type 1 gp41 are potent inhibitors of virus infection," *Proc. Natl. Acad. Sci. USA* 91:9770–9774 (1994).

William, Kelly P. et al., "Bioactive and nuclease–resistant 1–DNA ligand of vasopressin," *Proc. Natl. Acad. Sci. USA* 94:11285–11290 (1997).

Youngquist, R. Scott et al., "Generation and Screening of Combinatorial Peptide Libraries Designed for Rapid Sequencing by Mass Spectrometry," *J. Am. Chem. Soc.* 117:3900–3906 (1995).

```
CRYST1   49.500   49.500   55.300  90.00  90.00 120.00
ORIGX1       1.000000  0.000000  0.000000        0.00000
ORIGX2       0.000000  1.000000  0.000000        0.00000
ORIGX3       0.000000  0.000000  1.000000        0.00000
SCALE1       0.020202  0.011663 -0.000001        0.00000
SCALE2       0.000000  0.023327 -0.000001        0.00000
SCALE3       0.000000  0.000000  0.018083        0.00000
ATOM      1   C   ACE    0      19.211  14.270 -17.472  1.00 56.26
ATOM      2   O   ACE    0      19.488  14.580 -16.305  1.00 56.37
ATOM      3   CA  ACE    0      20.273  14.045 -18.531  1.00 56.01
ATOM      4   N   SER  546      17.955  14.014 -17.827  1.00 56.49
ATOM      5   H   SER  546      17.816  13.501 -18.652  1.00  0.00
ATOM      6   CA  SER  546      16.876  14.392 -16.942  1.00 56.15
ATOM      7   CB  SER  546      15.525  14.172 -17.546  1.00 56.05
ATOM      8   OG  SER  546      15.498  12.815 -17.842  1.00 57.84
ATOM      9   HG  SER  546      15.988  12.455 -18.582  1.00  0.00
ATOM     10   C   SER  546      16.909  13.631 -15.655  1.00 56.24
ATOM     11   O   SER  546      16.736  14.255 -14.615  1.00 57.67
ATOM     12   N   GLY  547      17.181  12.316 -15.724  1.00 55.59
ATOM     13   H   GLY  547      17.409  11.945 -16.618  1.00  0.00
ATOM     14   CA  GLY  547      17.202  11.414 -14.570  1.00 53.04
ATOM     15   C   GLY  547      18.299  11.783 -13.596  1.00 51.70
ATOM     16   O   GLY  547      18.147  11.667 -12.391  1.00 50.76
ATOM     17   N   ILE  548      19.399  12.280 -14.145  1.00 51.57
ATOM     18   H   ILE  548      19.445  12.272 -15.118  1.00  0.00
ATOM     19   CA  ILE  548      20.551  12.815 -13.425  1.00 52.14
ATOM     20   CB  ILE  548      21.693  13.043 -14.436  1.00 54.22
ATOM     21   CG2 ILE  548      22.861  13.705 -13.721  1.00 55.25
ATOM     22   CG1 ILE  548      22.120  11.712 -15.087  1.00 54.58
ATOM     23   CD  ILE  548      23.126  11.909 -16.234  1.00 56.29
ATOM     24   C   ILE  548      20.218  14.116 -12.696  1.00 51.31
ATOM     25   O   ILE  548      20.543  14.273 -11.519  1.00 50.83
ATOM     26   N   VAL  549      19.590  15.054 -13.393  1.00 50.93
ATOM     27   H   VAL  549      19.486  14.911 -14.360  1.00  0.00
ATOM     28   CA  VAL  549      19.093  16.291 -12.786  1.00 50.79
ATOM     29   CB  VAL  549      18.451  17.196 -13.841  1.00 52.28
ATOM     30   CG1 VAL  549      17.814  18.437 -13.226  1.00 54.97
ATOM     31   CG2 VAL  549      19.539  17.650 -14.780  1.00 51.05
ATOM     32   C   VAL  549      18.036  15.977 -11.726  1.00 50.36
ATOM     33   O   VAL  549      17.992  16.598 -10.674  1.00 51.60
ATOM     34   N   GLN  550      17.187  15.030 -12.001  1.00 49.13
ATOM     35   H   GLN  550      17.256  14.628 -12.913  1.00  0.00
ATOM     36   CA  GLN  550      16.176  14.508 -11.109  1.00 49.23
ATOM     37   CB  GLN  550      15.452  13.398 -11.814  1.00 52.96
ATOM     38   CG  GLN  550      13.929  13.475 -11.925  1.00 60.75
ATOM     39   CD  GLN  550      13.343  13.742 -10.585  1.00 65.31
ATOM     40   OE1 GLN  550      13.048  14.884 -10.294  1.00 71.73
ATOM     41   NE2 GLN  550      13.111  12.750  -9.753  1.00 67.42
ATOM     42   HE21 GLN 550      13.298  11.810 -10.020  1.00  0.00
ATOM     43   HE22 GLN 550      12.689  12.960  -8.892  1.00  0.00
ATOM     44   C   GLN  550      16.843  13.895  -9.861  1.00 48.50
ATOM     45   O   GLN  550      16.520  14.236  -8.736  1.00 47.94
ATOM     46   N   GLN  551      17.847  13.009 -10.014  1.00 47.87
ATOM     47   H   GLN  551      18.103  12.786 -10.928  1.00  0.00
ATOM     48   CA  GLN  551      18.607  12.368  -8.940  1.00 47.02
ATOM     49   CB  GLN  551      19.605  11.378  -9.582  1.00 45.66
ATOM     50   CG  GLN  551      20.600  10.535  -8.719  1.00 41.50
ATOM     51   CD  GLN  551      19.994   9.589  -7.719  1.00 39.83
```

FIG. 5A

| | | | | | | | |
|---|---|---|---|---|---|---|---|
| ATOM | 52 | OE1 | GLN | 551 | 18.955 | 9.872 | -7.134 | 1.00 42.03 |
| ATOM | 53 | NE2 | GLN | 551 | 20.573 | 8.430 | -7.469 | 1.00 34.15 |
| ATOM | 54 | HE21 | GLN | 551 | 21.382 | 8.205 | -7.988 | 1.00 0.00 |
| ATOM | 55 | HE22 | GLN | 551 | 20.183 | 7.817 | -6.808 | 1.00 0.00 |
| ATOM | 56 | C | GLN | 551 | 19.320 | 13.416 | -8.092 | 1.00 45.81 |
| ATOM | 57 | O | GLN | 551 | 19.330 | 13.334 | -6.868 | 1.00 46.09 |
| ATOM | 58 | N | GLN | 552 | 19.874 | 14.445 | -8.725 | 1.00 45.32 |
| ATOM | 59 | H | GLN | 552 | 19.818 | 14.442 | -9.707 | 1.00 0.00 |
| ATOM | 60 | CA | GLN | 552 | 20.538 | 15.562 | -8.041 | 1.00 44.72 |
| ATOM | 61 | CB | GLN | 552 | 21.115 | 16.542 | -9.078 | 1.00 46.04 |
| ATOM | 62 | CG | GLN | 552 | 22.500 | 16.015 | -9.433 | 1.00 50.92 |
| ATOM | 63 | CD | GLN | 552 | 23.257 | 16.787 | -10.486 | 1.00 54.67 |
| ATOM | 64 | OE1 | GLN | 552 | 22.658 | 17.525 | -11.260 | 1.00 59.31 |
| ATOM | 65 | NE2 | GLN | 552 | 24.575 | 16.670 | -10.575 | 1.00 56.36 |
| ATOM | 66 | HE21 | GLN | 552 | 25.079 | 16.087 | -9.993 | 1.00 0.00 |
| ATOM | 67 | HE22 | GLN | 552 | 24.996 | 17.210 | -11.277 | 1.00 0.00 |
| ATOM | 68 | C | GLN | 552 | 19.620 | 16.316 | -7.096 | 1.00 43.57 |
| ATOM | 69 | O | GLN | 552 | 19.987 | 16.732 | -6.006 | 1.00 41.76 |
| ATOM | 70 | N | ASN | 553 | 18.383 | 16.452 | -7.534 | 1.00 43.26 |
| ATOM | 71 | H | ASN | 553 | 18.168 | 16.200 | -8.470 | 1.00 0.00 |
| ATOM | 72 | CA | ASN | 553 | 17.350 | 17.053 | -6.728 | 1.00 43.57 |
| ATOM | 73 | CB | ASN | 553 | 16.050 | 17.238 | -7.509 | 1.00 46.51 |
| ATOM | 74 | CG | ASN | 553 | 15.095 | 18.168 | -6.802 | 1.00 51.48 |
| ATOM | 75 | OD1 | ASN | 553 | 15.256 | 18.608 | -5.669 | 1.00 59.01 |
| ATOM | 76 | ND2 | ASN | 553 | 14.006 | 18.540 | -7.412 | 1.00 57.62 |
| ATOM | 77 | HD21 | ASN | 553 | 13.822 | 18.181 | -8.313 | 1.00 0.00 |
| ATOM | 78 | HD22 | ASN | 553 | 13.333 | 19.036 | -6.902 | 1.00 0.00 |
| ATOM | 79 | C | ASN | 553 | 17.047 | 16.173 | -5.554 | 1.00 42.82 |
| ATOM | 80 | O | ASN | 553 | 16.914 | 16.649 | -4.433 | 1.00 43.18 |
| ATOM | 81 | N | ASN | 554 | 17.005 | 14.883 | -5.807 | 1.00 42.25 |
| ATOM | 82 | H | ASN | 554 | 17.137 | 14.573 | -6.736 | 1.00 0.00 |
| ATOM | 83 | CA | ASN | 554 | 16.731 | 13.930 | -4.736 | 1.00 43.15 |
| ATOM | 84 | CB | ASN | 554 | 16.534 | 12.538 | -5.331 | 1.00 44.49 |
| ATOM | 85 | CG | ASN | 554 | 15.340 | 12.520 | -6.239 | 1.00 48.97 |
| ATOM | 86 | OD1 | ASN | 554 | 14.277 | 13.033 | -5.925 | 1.00 51.91 |
| ATOM | 87 | ND2 | ASN | 554 | 15.485 | 12.022 | -7.460 | 1.00 52.70 |
| ATOM | 88 | HD21 | ASN | 554 | 16.321 | 11.585 | -7.671 | 1.00 0.00 |
| ATOM | 89 | HD22 | ASN | 554 | 14.691 | 11.924 | -8.059 | 1.00 0.00 |
| ATOM | 90 | C | ASN | 554 | 17.876 | 13.908 | -3.715 | 1.00 42.63 |
| ATOM | 91 | O | ASN | 554 | 17.628 | 13.893 | -2.508 | 1.00 42.65 |
| ATOM | 92 | N | LEU | 555 | 19.125 | 14.034 | -4.177 | 1.00 41.19 |
| ATOM | 93 | H | LEU | 555 | 19.245 | 14.101 | -5.145 | 1.00 0.00 |
| ATOM | 94 | CA | LEU | 555 | 20.270 | 14.065 | -3.310 | 1.00 39.88 |
| ATOM | 95 | CB | LEU | 555 | 21.556 | 13.984 | -4.115 | 1.00 37.85 |
| ATOM | 96 | CG | LEU | 555 | 21.762 | 12.724 | -4.945 | 1.00 38.85 |
| ATOM | 97 | CD1 | LEU | 555 | 23.106 | 12.783 | -5.687 | 1.00 39.10 |
| ATOM | 98 | CD2 | LEU | 555 | 21.643 | 11.526 | -4.019 | 1.00 36.44 |
| ATOM | 99 | C | LEU | 555 | 20.274 | 15.341 | -2.498 | 1.00 40.16 |
| ATOM | 100 | O | LEU | 555 | 20.383 | 15.280 | -1.272 | 1.00 40.42 |
| ATOM | 101 | N | LEU | 556 | 20.097 | 16.504 | -3.139 | 1.00 39.83 |
| ATOM | 102 | H | LEU | 556 | 20.042 | 16.470 | -4.118 | 1.00 0.00 |
| ATOM | 103 | CA | LEU | 556 | 20.056 | 17.800 | -2.490 | 1.00 39.00 |
| ATOM | 104 | CB | LEU | 556 | 19.769 | 18.896 | -3.504 | 1.00 37.52 |
| ATOM | 105 | CG | LEU | 556 | 19.826 | 20.327 | -2.982 | 1.00 35.51 |
| ATOM | 106 | CD1 | LEU | 556 | 21.227 | 20.634 | -2.595 | 1.00 38.30 |
| ATOM | 107 | CD2 | LEU | 556 | 19.383 | 21.304 | -4.051 | 1.00 35.56 |
| ATOM | 108 | C | LEU | 556 | 18.997 | 17.825 | -1.428 | 1.00 40.28 |
| ATOM | 109 | O | LEU | 556 | 19.251 | 18.290 | -0.226 | 1.00 40.24 |

FIG. 5B

| | | | | | | | | |
|---|---|---|---|---|---|---|---|---|
| ATOM | 110 | N | ARG | 557 | 17.823 | 17.292 | -1.689 | 1.00 41.01 |
| ATOM | 111 | H | ARG | 557 | 17.638 | 16.953 | -2.607 | 1.00  0.00 |
| ATOM | 112 | CA | ARG | 557 | 16.776 | 17.288 | -0.685 | 1.00 42.31 |
| ATOM | 113 | CB | ARG | 557 | 15.457 | 16.809 | -1.356 | 1.00 45.42 |
| ATOM | 114 | CG | ARG | 557 | 14.746 | 17.951 | -2.111 | 1.00 50.30 |
| ATOM | 115 | CD | ARG | 557 | 13.344 | 17.553 | -2.601 | 1.00 57.56 |
| ATOM | 116 | NE | ARG | 557 | 13.280 | 16.625 | -3.751 | 1.00 64.22 |
| ATOM | 117 | HE | ARG | 557 | 13.950 | 16.746 | -4.463 | 1.00  0.00 |
| ATOM | 118 | CZ | ARG | 557 | 12.355 | 15.631 | -3.918 | 1.00 63.91 |
| ATOM | 119 | NH1 | ARG | 557 | 11.397 | 15.396 | -3.011 | 1.00 64.47 |
| ATOM | 120 | HH11 | ARG | 557 | 11.350 | 15.933 | -2.167 | 1.00  0.00 |
| ATOM | 121 | HH12 | ARG | 557 | 10.752 | 14.634 | -3.142 | 1.00  0.00 |
| ATOM | 122 | NH2 | ARG | 557 | 12.335 | 14.867 | -5.036 | 1.00 59.98 |
| ATOM | 123 | HH21 | ARG | 557 | 12.994 | 15.016 | -5.779 | 1.00  0.00 |
| ATOM | 124 | HH22 | ARG | 557 | 11.659 | 14.126 | -5.135 | 1.00  0.00 |
| ATOM | 125 | C | ARG | 557 | 17.200 | 16.394 | 0.467 | 1.00 42.26 |
| ATOM | 126 | O | ARG | 557 | 17.012 | 16.740 | 1.622 | 1.00 42.69 |
| ATOM | 127 | N | ALA | 558 | 17.915 | 15.313 | 0.192 | 1.00 41.57 |
| ATOM | 128 | H | ALA | 558 | 18.173 | 15.144 | -0.746 | 1.00  0.00 |
| ATOM | 129 | CA | ALA | 558 | 18.387 | 14.409 | 1.226 | 1.00 41.10 |
| ATOM | 130 | CB | ALA | 558 | 19.030 | 13.199 | 0.587 | 1.00 41.90 |
| ATOM | 131 | C | ALA | 558 | 19.392 | 15.061 | 2.144 | 1.00 40.54 |
| ATOM | 132 | O | ALA | 558 | 19.295 | 14.930 | 3.360 | 1.00 39.05 |
| ATOM | 133 | N | ILE | 559 | 20.294 | 15.861 | 1.569 | 1.00 41.09 |
| ATOM | 134 | H | ILE | 559 | 20.262 | 15.968 | 0.586 | 1.00  0.00 |
| ATOM | 135 | CA | ILE | 559 | 21.309 | 16.634 | 2.316 | 1.00 40.49 |
| ATOM | 136 | CB | ILE | 559 | 22.333 | 17.310 | 1.315 | 1.00 37.40 |
| ATOM | 137 | CG2 | ILE | 559 | 23.294 | 18.213 | 2.061 | 1.00 36.22 |
| ATOM | 138 | CG1 | ILE | 559 | 23.112 | 16.223 | 0.558 | 1.00 35.03 |
| ATOM | 139 | CD | ILE | 559 | 23.944 | 16.723 | -0.634 | 1.00 29.22 |
| ATOM | 140 | C | ILE | 559 | 20.614 | 17.708 | 3.169 | 1.00 41.59 |
| ATOM | 141 | O | ILE | 559 | 20.961 | 17.946 | 4.334 | 1.00 41.89 |
| ATOM | 142 | N | GLU | 560 | 19.595 | 18.377 | 2.634 | 1.00 41.05 |
| ATOM | 143 | H | GLU | 560 | 19.338 | 18.191 | 1.696 | 1.00  0.00 |
| ATOM | 144 | CA | GLU | 560 | 18.927 | 19.411 | 3.378 | 1.00 41.53 |
| ATOM | 145 | CB | GLU | 560 | 17.950 | 20.139 | 2.504 | 1.00 42.94 |
| ATOM | 146 | CG | GLU | 560 | 18.559 | 20.916 | 1.342 | 1.00 49.98 |
| ATOM | 147 | CD | GLU | 560 | 17.569 | 21.635 | 0.403 | 1.00 56.47 |
| ATOM | 148 | OE1 | GLU | 560 | 16.353 | 21.580 | 0.624 | 1.00 58.21 |
| ATOM | 149 | OE2 | GLU | 560 | 18.018 | 22.257 | -0.566 | 1.00 56.22 |
| ATOM | 150 | C | GLU | 560 | 18.194 | 18.774 | 4.529 | 1.00 41.42 |
| ATOM | 151 | O | GLU | 560 | 18.199 | 19.290 | 5.659 | 1.00 42.58 |
| ATOM | 152 | N | ALA | 561 | 17.605 | 17.606 | 4.311 | 1.00 41.55 |
| ATOM | 153 | H | ALA | 561 | 17.617 | 17.230 | 3.403 | 1.00  0.00 |
| ATOM | 154 | CA | ALA | 561 | 16.886 | 16.905 | 5.362 | 1.00 41.77 |
| ATOM | 155 | CB | ALA | 561 | 16.221 | 15.671 | 4.797 | 1.00 39.29 |
| ATOM | 156 | C | ALA | 561 | 17.880 | 16.505 | 6.441 | 1.00 42.70 |
| ATOM | 157 | O | ALA | 561 | 17.661 | 16.726 | 7.641 | 1.00 42.40 |
| ATOM | 158 | N | GLN | 562 | 19.053 | 16.076 | 6.014 | 1.00 43.26 |
| ATOM | 159 | H | GLN | 562 | 19.263 | 16.023 | 5.043 | 1.00  0.00 |
| ATOM | 160 | CA | GLN | 562 | 20.042 | 15.666 | 6.986 | 1.00 43.97 |
| ATOM | 161 | CB | GLN | 562 | 21.194 | 14.960 | 6.319 | 1.00 45.81 |
| ATOM | 162 | CG | GLN | 562 | 20.703 | 13.620 | 5.857 | 1.00 48.45 |
| ATOM | 163 | CD | GLN | 562 | 21.844 | 12.875 | 5.276 | 1.00 52.27 |
| ATOM | 164 | OE1 | GLN | 562 | 22.693 | 13.426 | 4.578 | 1.00 54.50 |
| ATOM | 165 | NE2 | GLN | 562 | 21.828 | 11.590 | 5.556 | 1.00 54.42 |
| ATOM | 166 | HE21 | GLN | 562 | 21.094 | 11.248 | 6.104 | 1.00  0.00 |
| ATOM | 167 | HE22 | GLN | 562 | 22.558 | 11.067 | 5.175 | 1.00  0.00 |

FIG. 5C

| | | | | | | | | |
|---|---|---|---|---|---|---|---|---|
| ATOM | 168 | C | GLN | 562 | 20.607 | 16.819 | 7.771 | 1.00 43.53 |
| ATOM | 169 | O | GLN | 562 | 20.989 | 16.658 | 8.934 | 1.00 43.63 |
| ATOM | 170 | N | GLN | 563 | 20.651 | 17.976 | 7.121 | 1.00 42.95 |
| ATOM | 171 | H | GLN | 563 | 20.474 | 17.971 | 6.162 | 1.00 0.00 |
| ATOM | 172 | CA | GLN | 563 | 21.100 | 19.166 | 7.761 | 1.00 43.75 |
| ATOM | 173 | CB | GLN | 563 | 21.149 | 20.323 | 6.777 | 1.00 41.93 |
| ATOM | 174 | CG | GLN | 563 | 21.818 | 21.547 | 7.400 | 1.00 41.15 |
| ATOM | 175 | CD | GLN | 563 | 23.189 | 21.261 | 8.013 | 1.00 42.08 |
| ATOM | 176 | OE1 | GLN | 563 | 23.917 | 20.363 | 7.583 | 1.00 48.51 |
| ATOM | 177 | NE2 | GLN | 563 | 23.627 | 21.967 | 9.043 | 1.00 39.35 |
| ATOM | 178 | HE21 | GLN | 563 | 23.085 | 22.653 | 9.451 | 1.00 0.00 |
| ATOM | 179 | HE22 | GLN | 563 | 24.526 | 21.732 | 9.369 | 1.00 0.00 |
| ATOM | 180 | C | GLN | 563 | 20.156 | 19.484 | 8.886 | 1.00 44.90 |
| ATOM | 181 | O | GLN | 563 | 20.607 | 19.846 | 9.965 | 1.00 45.57 |
| ATOM | 182 | N | HIS | 564 | 18.842 | 19.364 | 8.714 | 1.00 46.08 |
| ATOM | 183 | H | HIS | 564 | 18.535 | 19.251 | 7.783 | 1.00 0.00 |
| ATOM | 184 | CA | HIS | 564 | 17.909 | 19.582 | 9.830 | 1.00 47.34 |
| ATOM | 185 | CB | HIS | 564 | 16.508 | 19.405 | 9.372 | 1.00 52.29 |
| ATOM | 186 | CG | HIS | 564 | 16.122 | 20.497 | 8.389 | 1.00 58.12 |
| ATOM | 187 | CD2 | HIS | 564 | 16.858 | 21.617 | 8.051 | 1.00 61.99 |
| ATOM | 188 | ND1 | HIS | 564 | 15.024 | 20.554 | 7.683 | 1.00 63.16 |
| ATOM | 189 | HD1 | HIS | 564 | 14.318 | 19.929 | 7.750 | 1.00 0.00 |
| ATOM | 190 | CE1 | HIS | 564 | 15.029 | 21.609 | 6.945 | 1.00 62.90 |
| ATOM | 191 | NE2 | HIS | 564 | 16.140 | 22.240 | 7.177 | 1.00 62.40 |
| ATOM | 192 | HE2 | HIS | 564 | 16.408 | 23.027 | 6.657 | 1.00 0.00 |
| ATOM | 193 | C | HIS | 564 | 18.133 | 18.647 | 10.985 | 1.00 46.35 |
| ATOM | 194 | O | HIS | 564 | 18.167 | 19.105 | 12.118 | 1.00 45.28 |
| ATOM | 195 | N | LEU | 565 | 18.352 | 17.382 | 10.651 | 1.00 46.30 |
| ATOM | 196 | H | LEU | 565 | 18.325 | 17.139 | 9.702 | 1.00 0.00 |
| ATOM | 197 | CA | LEU | 565 | 18.728 | 16.389 | 11.627 | 1.00 47.50 |
| ATOM | 198 | CB | LEU | 565 | 18.955 | 15.028 | 10.980 | 1.00 48.98 |
| ATOM | 199 | CG | LEU | 565 | 17.893 | 13.938 | 10.810 | 1.00 50.24 |
| ATOM | 200 | CD1 | LEU | 565 | 18.612 | 12.580 | 10.876 | 1.00 49.28 |
| ATOM | 201 | CD2 | LEU | 565 | 16.843 | 13.988 | 11.920 | 1.00 52.14 |
| ATOM | 202 | C | LEU | 565 | 20.023 | 16.771 | 12.360 | 1.00 47.96 |
| ATOM | 203 | O | LEU | 565 | 20.106 | 16.694 | 13.603 | 1.00 47.27 |
| ATOM | 204 | N | LEU | 566 | 21.033 | 17.258 | 11.622 | 1.00 47.51 |
| ATOM | 205 | H | LEU | 566 | 20.921 | 17.339 | 10.656 | 1.00 0.00 |
| ATOM | 206 | CA | LEU | 566 | 22.278 | 17.718 | 12.229 | 1.00 48.90 |
| ATOM | 207 | CB | LEU | 566 | 23.299 | 18.205 | 11.144 | 1.00 50.19 |
| ATOM | 208 | CG | LEU | 566 | 24.223 | 17.163 | 10.521 | 1.00 50.83 |
| ATOM | 209 | CD1 | LEU | 566 | 24.767 | 17.627 | 9.151 | 1.00 45.73 |
| ATOM | 210 | CD2 | LEU | 566 | 25.295 | 16.848 | 11.579 | 1.00 50.85 |
| ATOM | 211 | C | LEU | 566 | 22.041 | 18.835 | 13.232 | 1.00 48.39 |
| ATOM | 212 | O | LEU | 566 | 22.563 | 18.779 | 14.346 | 1.00 47.61 |
| ATOM | 213 | N | GLN | 567 | 21.182 | 19.797 | 12.902 | 1.00 48.03 |
| ATOM | 214 | H | GLN | 567 | 20.769 | 19.768 | 12.006 | 1.00 0.00 |
| ATOM | 215 | CA | GLN | 567 | 20.839 | 20.897 | 13.794 | 1.00 48.69 |
| ATOM | 216 | CB | GLN | 567 | 19.940 | 21.927 | 13.071 | 1.00 49.47 |
| ATOM | 217 | CG | GLN | 567 | 20.632 | 22.647 | 11.906 | 1.00 56.49 |
| ATOM | 218 | CD | GLN | 567 | 21.964 | 23.290 | 12.278 | 1.00 63.24 |
| ATOM | 219 | OE1 | GLN | 567 | 22.393 | 23.265 | 13.426 | 1.00 66.99 |
| ATOM | 220 | NE2 | GLN | 567 | 22.723 | 23.924 | 11.394 | 1.00 68.66 |
| ATOM | 221 | HE21 | GLN | 567 | 22.514 | 24.033 | 10.471 | 1.00 0.00 |
| ATOM | 222 | HE22 | GLN | 567 | 23.539 | 24.303 | 11.833 | 1.00 0.00 |
| ATOM | 223 | C | GLN | 567 | 20.124 | 20.425 | 15.041 | 1.00 48.44 |
| ATOM | 224 | O | GLN | 567 | 20.379 | 20.878 | 16.165 | 1.00 48.89 |
| ATOM | 225 | N | LEU | 568 | 19.313 | 19.365 | 14.871 | 1.00 48.05 |

FIG. 5D

| | | | | | | | | | |
|---|---|---|---|---|---|---|---|---|---|
| ATOM | 226 | H | LEU | 568 | 19.352 | 18.869 | 14.024 | 1.00 | 0.00 |
| ATOM | 227 | CA | LEU | 568 | 18.513 | 18.907 | 15.980 | 1.00 | 47.97 |
| ATOM | 228 | CB | LEU | 568 | 17.399 | 18.019 | 15.472 | 1.00 | 47.11 |
| ATOM | 229 | CG | LEU | 568 | 16.441 | 18.651 | 14.453 | 1.00 | 52.05 |
| ATOM | 230 | CD1 | LEU | 568 | 15.376 | 17.669 | 14.033 | 1.00 | 49.38 |
| ATOM | 231 | CD2 | LEU | 568 | 15.844 | 19.917 | 15.044 | 1.00 | 53.06 |
| ATOM | 232 | C | LEU | 568 | 19.410 | 18.201 | 16.958 | 1.00 | 47.65 |
| ATOM | 233 | O | LEU | 568 | 19.319 | 18.457 | 18.167 | 1.00 | 48.06 |
| ATOM | 234 | N | THR | 569 | 20.343 | 17.385 | 16.474 | 1.00 | 47.68 |
| ATOM | 235 | H | THR | 569 | 20.365 | 17.208 | 15.510 | 1.00 | 0.00 |
| ATOM | 236 | CA | THR | 569 | 21.300 | 16.706 | 17.345 | 1.00 | 46.82 |
| ATOM | 237 | CB | THR | 569 | 22.196 | 15.706 | 16.513 | 1.00 | 48.47 |
| ATOM | 238 | OG1 | THR | 569 | 22.896 | 16.453 | 15.512 | 1.00 | 50.39 |
| ATOM | 239 | HG1 | THR | 569 | 22.309 | 16.916 | 14.917 | 1.00 | 0.00 |
| ATOM | 240 | CG2 | THR | 569 | 21.367 | 14.574 | 15.887 | 1.00 | 45.02 |
| ATOM | 241 | C | THR | 569 | 22.179 | 17.733 | 18.051 | 1.00 | 46.78 |
| ATOM | 242 | O | THR | 569 | 22.428 | 17.562 | 19.238 | 1.00 | 46.53 |
| ATOM | 243 | N | VAL | 570 | 22.568 | 18.851 | 17.411 | 1.00 | 46.51 |
| ATOM | 244 | H | VAL | 570 | 22.267 | 19.018 | 16.480 | 1.00 | 0.00 |
| ATOM | 245 | CA | VAL | 570 | 23.388 | 19.879 | 18.056 | 1.00 | 46.07 |
| ATOM | 246 | CB | VAL | 570 | 23.824 | 20.975 | 17.067 | 1.00 | 46.87 |
| ATOM | 247 | CG1 | VAL | 570 | 24.628 | 22.078 | 17.767 | 1.00 | 43.56 |
| ATOM | 248 | CG2 | VAL | 570 | 24.698 | 20.324 | 16.003 | 1.00 | 47.58 |
| ATOM | 249 | C | VAL | 570 | 22.584 | 20.543 | 19.173 | 1.00 | 46.10 |
| ATOM | 250 | O | VAL | 570 | 23.109 | 20.791 | 20.268 | 1.00 | 46.19 |
| ATOM | 251 | N | TRP | 571 | 21.311 | 20.824 | 18.901 | 1.00 | 44.96 |
| ATOM | 252 | H | TRP | 571 | 20.993 | 20.625 | 17.998 | 1.00 | 0.00 |
| ATOM | 253 | CA | TRP | 571 | 20.448 | 21.354 | 19.916 | 1.00 | 45.54 |
| ATOM | 254 | CB | TRP | 571 | 19.025 | 21.547 | 19.422 | 1.00 | 45.68 |
| ATOM | 255 | CG | TRP | 571 | 18.046 | 21.979 | 20.538 | 1.00 | 47.31 |
| ATOM | 256 | CD2 | TRP | 571 | 17.291 | 21.171 | 21.401 | 1.00 | 48.92 |
| ATOM | 257 | CE2 | TRP | 571 | 16.630 | 22.132 | 22.175 | 1.00 | 47.99 |
| ATOM | 258 | CE3 | TRP | 571 | 17.056 | 19.805 | 21.674 | 1.00 | 48.37 |
| ATOM | 259 | CD1 | TRP | 571 | 17.853 | 23.309 | 20.778 | 1.00 | 47.86 |
| ATOM | 260 | NE1 | TRP | 571 | 16.991 | 23.361 | 21.767 | 1.00 | 47.92 |
| ATOM | 261 | HE1 | TRP | 571 | 16.632 | 24.201 | 22.162 | 1.00 | 0.00 |
| ATOM | 262 | CZ2 | TRP | 571 | 15.742 | 21.753 | 23.189 | 1.00 | 46.81 |
| ATOM | 263 | CZ3 | TRP | 571 | 16.181 | 19.419 | 22.697 | 1.00 | 46.38 |
| ATOM | 264 | CH2 | TRP | 571 | 15.524 | 20.395 | 23.451 | 1.00 | 47.44 |
| ATOM | 265 | C | TRP | 571 | 20.408 | 20.357 | 21.079 | 1.00 | 45.70 |
| ATOM | 266 | O | TRP | 571 | 20.466 | 20.796 | 22.237 | 1.00 | 46.48 |
| ATOM | 267 | N | GLY | 572 | 20.356 | 19.036 | 20.842 | 1.00 | 45.29 |
| ATOM | 268 | H | GLY | 572 | 20.483 | 18.736 | 19.917 | 1.00 | 0.00 |
| ATOM | 269 | CA | GLY | 572 | 20.270 | 18.034 | 21.892 | 1.00 | 44.49 |
| ATOM | 270 | C | GLY | 572 | 21.532 | 18.044 | 22.719 | 1.00 | 44.03 |
| ATOM | 271 | O | GLY | 572 | 21.491 | 18.102 | 23.948 | 1.00 | 43.66 |
| ATOM | 272 | N | ILE | 573 | 22.671 | 18.122 | 22.031 | 1.00 | 44.11 |
| ATOM | 273 | H | ILE | 573 | 22.603 | 18.229 | 21.056 | 1.00 | 0.00 |
| ATOM | 274 | CA | ILE | 573 | 23.986 | 18.156 | 22.666 | 1.00 | 44.64 |
| ATOM | 275 | CB | ILE | 573 | 25.125 | 18.159 | 21.622 | 1.00 | 44.82 |
| ATOM | 276 | CG2 | ILE | 573 | 26.482 | 18.303 | 22.325 | 1.00 | 44.82 |
| ATOM | 277 | CG1 | ILE | 573 | 25.094 | 16.885 | 20.810 | 1.00 | 43.85 |
| ATOM | 278 | CD | ILE | 573 | 26.010 | 16.983 | 19.585 | 1.00 | 44.87 |
| ATOM | 279 | C | ILE | 573 | 24.148 | 19.402 | 23.527 | 1.00 | 45.83 |
| ATOM | 280 | O | ILE | 573 | 24.571 | 19.300 | 24.666 | 1.00 | 46.58 |
| ATOM | 281 | N | LYS | 574 | 23.840 | 20.594 | 23.044 | 1.00 | 46.57 |
| ATOM | 282 | H | LYS | 574 | 23.447 | 20.634 | 22.137 | 1.00 | 0.00 |
| ATOM | 283 | CA | LYS | 574 | 24.001 | 21.819 | 23.817 | 1.00 | 47.39 |

FIG. 5E

| | | | | | | | | |
|---|---|---|---|---|---|---|---|---|
| ATOM | 284 | CB | LYS | 574 | 23.679 | 23.041 | 22.944 | 1.00 47.81 |
| ATOM | 285 | CG | LYS | 574 | 24.626 | 23.233 | 21.776 | 1.00 47.81 |
| ATOM | 286 | CD | LYS | 574 | 24.343 | 24.597 | 21.117 | 1.00 49.66 |
| ATOM | 287 | CE | LYS | 574 | 25.235 | 24.786 | 19.879 | 1.00 57.06 |
| ATOM | 288 | NZ | LYS | 574 | 25.047 | 26.026 | 19.167 | 1.00 51.95 |
| ATOM | 289 | HZ1 | LYS | 574 | 25.302 | 26.787 | 19.816 | 1.00  0.00 |
| ATOM | 290 | HZ2 | LYS | 574 | 24.056 | 26.097 | 18.850 | 1.00  0.00 |
| ATOM | 291 | HZ3 | LYS | 574 | 25.671 | 26.035 | 18.326 | 1.00  0.00 |
| ATOM | 292 | C | LYS | 574 | 23.075 | 21.810 | 25.027 | 1.00 47.64 |
| ATOM | 293 | O | LYS | 574 | 23.456 | 22.221 | 26.103 | 1.00 47.42 |
| ATOM | 294 | N | GLN | 575 | 21.863 | 21.301 | 24.898 | 1.00 47.76 |
| ATOM | 295 | H | GLN | 575 | 21.606 | 20.942 | 24.016 | 1.00  0.00 |
| ATOM | 296 | CA | GLN | 575 | 20.947 | 21.160 | 26.010 | 1.00 49.56 |
| ATOM | 297 | CB | GLN | 575 | 19.690 | 20.480 | 25.617 | 1.00 51.27 |
| ATOM | 298 | CG | GLN | 575 | 18.703 | 21.312 | 24.814 | 1.00 53.77 |
| ATOM | 299 | CD | GLN | 575 | 18.143 | 22.472 | 25.591 | 1.00 56.45 |
| ATOM | 300 | OE1 | GLN | 575 | 17.537 | 22.387 | 26.656 | 1.00 59.04 |
| ATOM | 301 | NE2 | GLN | 575 | 18.305 | 23.636 | 25.024 | 1.00 57.29 |
| ATOM | 302 | HE21 | GLN | 575 | 18.755 | 23.713 | 24.154 | 1.00  0.00 |
| ATOM | 303 | HE22 | GLN | 575 | 17.915 | 24.394 | 25.512 | 1.00  0.00 |
| ATOM | 304 | C | GLN | 575 | 21.523 | 20.277 | 27.101 | 1.00 50.70 |
| ATOM | 305 | O | GLN | 575 | 21.530 | 20.599 | 28.288 | 1.00 50.85 |
| ATOM | 306 | N | LEU | 576 | 22.054 | 19.126 | 26.704 | 1.00 52.27 |
| ATOM | 307 | H | LEU | 576 | 22.073 | 18.904 | 25.743 | 1.00  0.00 |
| ATOM | 308 | CA | LEU | 576 | 22.609 | 18.227 | 27.703 | 1.00 54.14 |
| ATOM | 309 | CB | LEU | 576 | 22.892 | 16.841 | 27.117 | 1.00 51.84 |
| ATOM | 310 | CG | LEU | 576 | 21.688 | 16.085 | 26.553 | 1.00 52.59 |
| ATOM | 311 | CD1 | LEU | 576 | 22.138 | 14.746 | 26.001 | 1.00 50.01 |
| ATOM | 312 | CD2 | LEU | 576 | 20.643 | 15.931 | 27.638 | 1.00 51.10 |
| ATOM | 313 | C | LEU | 576 | 23.887 | 18.797 | 28.277 | 1.00 55.59 |
| ATOM | 314 | O | LEU | 576 | 24.135 | 18.667 | 29.472 | 1.00 55.72 |
| ATOM | 315 | N | GLN | 577 | 24.692 | 19.489 | 27.474 | 1.00 57.40 |
| ATOM | 316 | H | GLN | 577 | 24.455 | 19.535 | 26.530 | 1.00  0.00 |
| ATOM | 317 | CA | GLN | 577 | 25.921 | 20.110 | 27.929 | 1.00 59.81 |
| ATOM | 318 | CB | GLN | 577 | 26.708 | 20.620 | 26.730 | 1.00 57.05 |
| ATOM | 319 | CG | GLN | 577 | 28.060 | 21.087 | 27.186 | 1.00 58.22 |
| ATOM | 320 | CD | GLN | 577 | 28.180 | 22.600 | 27.330 | 1.00 60.01 |
| ATOM | 321 | OE1 | GLN | 577 | 27.202 | 23.340 | 27.358 | 1.00 60.52 |
| ATOM | 322 | NE2 | GLN | 577 | 29.385 | 23.134 | 27.363 | 1.00 61.54 |
| ATOM | 323 | HE21 | GLN | 577 | 30.164 | 22.554 | 27.335 | 1.00  0.00 |
| ATOM | 324 | HE22 | GLN | 577 | 29.399 | 24.107 | 27.430 | 1.00  0.00 |
| ATOM | 325 | C | GLN | 577 | 25.672 | 21.245 | 28.915 | 1.00 62.47 |
| ATOM | 326 | O | GLN | 577 | 26.453 | 21.404 | 29.852 | 1.00 62.30 |
| ATOM | 327 | N | ALA | 578 | 24.584 | 21.997 | 28.775 | 1.00 65.04 |
| ATOM | 328 | H | ALA | 578 | 23.987 | 21.810 | 28.016 | 1.00  0.00 |
| ATOM | 329 | CA | ALA | 578 | 24.312 | 23.121 | 29.647 | 1.00 67.52 |
| ATOM | 330 | CB | ALA | 578 | 23.056 | 23.840 | 29.207 | 1.00 66.26 |
| ATOM | 331 | C | ALA | 578 | 24.101 | 22.643 | 31.062 | 1.00 69.93 |
| ATOM | 332 | O | ALA | 578 | 24.379 | 23.346 | 32.025 | 1.00 70.22 |
| ATOM | 333 | N | ARG | 579 | 23.604 | 21.407 | 31.195 | 1.00 72.80 |
| ATOM | 334 | H | ARG | 579 | 23.402 | 20.913 | 30.376 | 1.00  0.00 |
| ATOM | 335 | CA | ARG | 579 | 23.277 | 20.834 | 32.491 | 1.00 76.15 |
| ATOM | 336 | CB | ARG | 579 | 21.939 | 20.093 | 32.368 | 1.00 77.38 |
| ATOM | 337 | CG | ARG | 579 | 20.802 | 20.968 | 31.853 | 1.00 80.38 |
| ATOM | 338 | CD | ARG | 579 | 19.487 | 20.222 | 31.726 | 1.00 84.49 |
| ATOM | 339 | NE | ARG | 579 | 18.438 | 21.069 | 31.147 | 1.00 88.84 |
| ATOM | 340 | HE | ARG | 579 | 18.509 | 22.039 | 31.265 | 1.00  0.00 |
| ATOM | 341 | CZ | ARG | 579 | 17.385 | 20.587 | 30.457 | 1.00 91.52 |

FIG. 5F

| | | | | | | | | |
|---|---|---|---|---|---|---|---|---|
| ATOM | 342 | NH1 | ARG | 579 | 17.230 | 19.303 | 30.253 | 1.00 94.12 |
| ATOM | 343 | HH11 | ARG | 579 | 17.879 | 18.631 | 30.623 | 1.00  0.00 |
| ATOM | 344 | HH12 | ARG | 579 | 16.423 | 18.975 | 29.754 | 1.00  0.00 |
| ATOM | 345 | NH2 | ARG | 579 | 16.430 | 21.352 | 29.931 | 1.00 90.71 |
| ATOM | 346 | HH21 | ARG | 579 | 16.473 | 22.346 | 30.014 | 1.00  0.00 |
| ATOM | 347 | HH22 | ARG | 579 | 15.675 | 20.923 | 29.427 | 1.00  0.00 |
| ATOM | 348 | C | ARG | 579 | 24.297 | 19.924 | 33.116 | 1.00 77.71 |
| ATOM | 349 | O | ARG | 579 | 24.155 | 19.391 | 34.212 | 1.00 78.20 |
| ATOM | 350 | N | ILE | 580 | 25.362 | 19.713 | 32.371 | 1.00 79.12 |
| ATOM | 351 | H | ILE | 580 | 25.445 | 20.241 | 31.548 | 1.00  0.00 |
| ATOM | 352 | CA | ILE | 580 | 26.445 | 18.772 | 32.675 | 1.00 81.05 |
| ATOM | 353 | CB | ILE | 580 | 26.246 | 17.503 | 31.784 | 1.00 80.80 |
| ATOM | 354 | CG2 | ILE | 580 | 27.451 | 16.589 | 31.650 | 1.00 78.88 |
| ATOM | 355 | CG1 | ILE | 580 | 25.193 | 16.697 | 32.429 | 1.00 84.04 |
| ATOM | 356 | CD | ILE | 580 | 24.516 | 16.191 | 31.215 | 1.00 86.00 |
| ATOM | 357 | C | ILE | 580 | 27.660 | 19.565 | 32.303 | 1.00 82.42 |
| ATOM | 358 | O | ILE | 580 | 28.531 | 19.018 | 31.659 | 1.00 83.59 |
| ATOM | 359 | N | LEU | 581 | 27.698 | 20.865 | 32.557 | 1.00 83.28 |
| ATOM | 360 | H | LEU | 581 | 26.907 | 21.292 | 32.938 | 1.00  0.00 |
| ATOM | 361 | CA | LEU | 581 | 28.887 | 21.706 | 32.347 | 1.00 83.95 |
| ATOM | 362 | CB | LEU | 581 | 29.461 | 21.581 | 30.920 | 1.00 82.81 |
| ATOM | 363 | CG | LEU | 581 | 30.924 | 21.079 | 30.935 | 1.00 80.52 |
| ATOM | 364 | CD1 | LEU | 581 | 31.242 | 20.050 | 32.038 | 1.00 78.52 |
| ATOM | 365 | CD2 | LEU | 581 | 31.148 | 20.566 | 29.548 | 1.00 80.15 |
| ATOM | 366 | C | LEU | 581 | 28.597 | 23.173 | 32.668 | 1.00 84.95 |
| ATOM | 367 | OT1 | LEU | 581 | 27.778 | 23.359 | 33.577 | 1.00 88.48 |
| ATOM | 368 | OT2 | LEU | 581 | 29.255 | 24.081 | 32.155 | 1.00 82.98 |
| ATOM | 369 | C | ACE | 627 | 11.678 | 19.563 | 23.916 | 1.00 59.46 |
| ATOM | 370 | O | ACE | 627 | 11.509 | 19.280 | 22.723 | 1.00 59.59 |
| ATOM | 371 | CA | ACE | 627 | 11.401 | 20.961 | 24.478 | 1.00 59.14 |
| ATOM | 372 | N | TRP | 628 | 11.939 | 18.567 | 24.754 | 1.00 59.45 |
| ATOM | 373 | H | TRP | 628 | 11.881 | 18.708 | 25.724 | 1.00  0.00 |
| ATOM | 374 | CA | TRP | 628 | 12.345 | 17.262 | 24.249 | 1.00 58.85 |
| ATOM | 375 | CB | TRP | 628 | 12.905 | 16.491 | 25.449 | 1.00 56.27 |
| ATOM | 376 | CG | TRP | 628 | 14.324 | 16.987 | 25.710 | 1.00 52.28 |
| ATOM | 377 | CD2 | TRP | 628 | 15.466 | 16.576 | 25.059 | 1.00 52.52 |
| ATOM | 378 | CE2 | TRP | 628 | 16.442 | 17.360 | 25.680 | 1.00 53.25 |
| ATOM | 379 | CE3 | TRP | 628 | 15.833 | 15.676 | 24.060 | 1.00 49.19 |
| ATOM | 380 | CD1 | TRP | 628 | 14.560 | 17.945 | 26.654 | 1.00 52.77 |
| ATOM | 381 | NE1 | TRP | 628 | 15.852 | 18.149 | 26.605 | 1.00 53.20 |
| ATOM | 382 | HE1 | TRP | 628 | 16.338 | 18.759 | 27.208 | 1.00  0.00 |
| ATOM | 383 | CZ2 | TRP | 628 | 17.793 | 17.256 | 25.297 | 1.00 50.70 |
| ATOM | 384 | CZ3 | TRP | 628 | 17.180 | 15.570 | 23.699 | 1.00 49.98 |
| ATOM | 385 | CH2 | TRP | 628 | 18.158 | 16.350 | 24.304 | 1.00 47.48 |
| ATOM | 386 | C | TRP | 628 | 11.305 | 16.438 | 23.468 | 1.00 59.28 |
| ATOM | 387 | O | TRP | 628 | 11.646 | 15.639 | 22.589 | 1.00 59.31 |
| ATOM | 388 | N | MET | 629 |  9.992 | 16.635 | 23.651 | 1.00 59.74 |
| ATOM | 389 | H | MET | 629 |  9.728 | 17.227 | 24.356 | 1.00  0.00 |
| ATOM | 390 | CA | MET | 629 |  9.041 | 15.870 | 22.852 | 1.00 60.58 |
| ATOM | 391 | CB | MET | 629 |  7.644 | 15.848 | 23.489 | 1.00 63.71 |
| ATOM | 392 | CG | MET | 629 |  7.364 | 16.823 | 24.657 | 1.00 68.98 |
| ATOM | 393 | SD | MET | 629 |  6.220 | 16.291 | 25.948 | 1.00 72.59 |
| ATOM | 394 | CE | MET | 629 |  4.843 | 16.119 | 24.844 | 1.00 72.83 |
| ATOM | 395 | C | MET | 629 |  8.978 | 16.434 | 21.441 | 1.00 59.92 |
| ATOM | 396 | O | MET | 629 |  8.878 | 15.698 | 20.450 | 1.00 59.94 |
| ATOM | 397 | N | GLU | 630 |  9.151 | 17.749 | 21.302 | 1.00 59.19 |
| ATOM | 398 | H | GLU | 630 |  9.289 | 18.287 | 22.086 | 1.00  0.00 |
| ATOM | 399 | CA | GLU | 630 |  9.179 | 18.350 | 19.990 | 1.00 59.94 |

FIG. 5G

| ATOM | 400 | CB | GLU | 630 | 9.192 | 19.876 | 20.063 | 1.00 | 62.30 |
|------|-----|------|-----|-----|--------|--------|--------|------|-------|
| ATOM | 401 | CG | GLU | 630 | 9.263 | 20.558 | 18.693 | 1.00 | 66.55 |
| ATOM | 402 | CD | GLU | 630 | 8.214 | 20.271 | 17.616 | 1.00 | 69.57 |
| ATOM | 403 | OE1 | GLU | 630 | 7.325 | 19.430 | 17.788 | 1.00 | 71.12 |
| ATOM | 404 | OE2 | GLU | 630 | 8.304 | 20.921 | 16.577 | 1.00 | 71.20 |
| ATOM | 405 | C | GLU | 630 | 10.391 | 17.903 | 19.195 | 1.00 | 59.73 |
| ATOM | 406 | O | GLU | 630 | 10.317 | 17.666 | 17.988 | 1.00 | 58.71 |
| ATOM | 407 | N | TRP | 631 | 11.517 | 17.795 | 19.893 | 1.00 | 60.09 |
| ATOM | 408 | H | TRP | 631 | 11.515 | 18.006 | 20.858 | 1.00 | 0.00 |
| ATOM | 409 | CA | TRP | 631 | 12.758 | 17.353 | 19.309 | 1.00 | 60.33 |
| ATOM | 410 | CB | TRP | 631 | 13.836 | 17.478 | 20.395 | 1.00 | 56.29 |
| ATOM | 411 | CG | TRP | 631 | 15.206 | 16.925 | 19.960 | 1.00 | 54.47 |
| ATOM | 412 | CD2 | TRP | 631 | 15.644 | 15.637 | 20.169 | 1.00 | 50.58 |
| ATOM | 413 | CE2 | TRP | 631 | 16.924 | 15.687 | 19.621 | 1.00 | 50.81 |
| ATOM | 414 | CE3 | TRP | 631 | 15.169 | 14.490 | 20.782 | 1.00 | 44.66 |
| ATOM | 415 | CD1 | TRP | 631 | 16.103 | 17.708 | 19.291 | 1.00 | 54.11 |
| ATOM | 416 | NE1 | TRP | 631 | 17.137 | 16.928 | 19.120 | 1.00 | 53.39 |
| ATOM | 417 | HE1 | TRP | 631 | 17.965 | 17.239 | 18.688 | 1.00 | 0.00 |
| ATOM | 418 | CZ2 | TRP | 631 | 17.755 | 14.558 | 19.662 | 1.00 | 48.32 |
| ATOM | 419 | CZ3 | TRP | 631 | 15.995 | 13.360 | 20.809 | 1.00 | 45.04 |
| ATOM | 420 | CH2 | TRP | 631 | 17.274 | 13.377 | 20.242 | 1.00 | 45.24 |
| ATOM | 421 | C | TRP | 631 | 12.541 | 15.931 | 18.819 | 1.00 | 61.17 |
| ATOM | 422 | O | TRP | 631 | 12.869 | 15.598 | 17.708 | 1.00 | 61.33 |
| ATOM | 423 | N | ASP | 632 | 11.873 | 15.089 | 19.562 | 1.00 | 62.54 |
| ATOM | 424 | H | ASP | 632 | 11.482 | 15.413 | 20.422 | 1.00 | 0.00 |
| ATOM | 425 | CA | ASP | 632 | 11.600 | 13.733 | 19.160 | 1.00 | 64.59 |
| ATOM | 426 | CB | ASP | 632 | 10.801 | 13.059 | 20.184 | 1.00 | 66.75 |
| ATOM | 427 | CG | ASP | 632 | 11.553 | 11.867 | 20.759 | 1.00 | 70.81 |
| ATOM | 428 | OD1 | ASP | 632 | 11.763 | 10.875 | 20.036 | 1.00 | 73.19 |
| ATOM | 429 | OD2 | ASP | 632 | 11.864 | 12.009 | 21.934 | 1.00 | 73.17 |
| ATOM | 430 | C | ASP | 632 | 10.784 | 13.653 | 17.877 | 1.00 | 65.43 |
| ATOM | 431 | O | ASP | 632 | 11.049 | 12.839 | 16.989 | 1.00 | 65.87 |
| ATOM | 432 | N | ARG | 633 | 9.741 | 14.481 | 17.788 | 1.00 | 65.95 |
| ATOM | 433 | H | ARG | 633 | 9.604 | 15.123 | 18.523 | 1.00 | 0.00 |
| ATOM | 434 | CA | ARG | 633 | 8.846 | 14.452 | 16.645 | 1.00 | 66.10 |
| ATOM | 435 | CB | ARG | 633 | 7.586 | 15.329 | 16.804 | 1.00 | 70.93 |
| ATOM | 436 | CG | ARG | 633 | 6.473 | 15.063 | 17.832 | 1.00 | 77.51 |
| ATOM | 437 | CD | ARG | 633 | 5.742 | 16.383 | 18.096 | 1.00 | 83.59 |
| ATOM | 438 | NE | ARG | 633 | 5.101 | 16.320 | 19.404 | 1.00 | 90.92 |
| ATOM | 439 | HE | ARG | 633 | 5.536 | 15.785 | 20.096 | 1.00 | 0.00 |
| ATOM | 440 | CZ | ARG | 633 | 3.946 | 16.916 | 19.715 | 1.00 | 96.53 |
| ATOM | 441 | NH1 | ARG | 633 | 3.295 | 17.634 | 18.820 | 1.00 | 99.82 |
| ATOM | 442 | HH11 | ARG | 633 | 3.715 | 17.801 | 17.918 | 1.00 | 0.00 |
| ATOM | 443 | HH12 | ARG | 633 | 2.486 | 18.174 | 19.079 | 1.00 | 0.00 |
| ATOM | 444 | NH2 | ARG | 633 | 3.344 | 16.753 | 20.891 | 1.00 | 99.12 |
| ATOM | 445 | HH21 | ARG | 633 | 3.713 | 16.130 | 21.573 | 1.00 | 0.00 |
| ATOM | 446 | HH22 | ARG | 633 | 2.491 | 17.256 | 21.077 | 1.00 | 0.00 |
| ATOM | 447 | C | ARG | 633 | 9.628 | 15.030 | 15.464 | 1.00 | 64.57 |
| ATOM | 448 | O | ARG | 633 | 9.583 | 14.449 | 14.377 | 1.00 | 64.74 |
| ATOM | 449 | N | GLU | 634 | 10.397 | 16.100 | 15.645 | 1.00 | 62.76 |
| ATOM | 450 | H | GLU | 634 | 10.437 | 16.483 | 16.554 | 1.00 | 0.00 |
| ATOM | 451 | CA | GLU | 634 | 11.159 | 16.676 | 14.569 | 1.00 | 61.33 |
| ATOM | 452 | CB | GLU | 634 | 11.823 | 17.935 | 14.998 | 1.00 | 61.32 |
| ATOM | 453 | CG | GLU | 634 | 10.784 | 19.053 | 14.903 | 1.00 | 68.08 |
| ATOM | 454 | CD | GLU | 634 | 11.401 | 20.433 | 14.751 | 1.00 | 74.96 |
| ATOM | 455 | OE1 | GLU | 634 | 12.353 | 20.598 | 13.977 | 1.00 | 76.47 |
| ATOM | 456 | OE2 | GLU | 634 | 10.902 | 21.363 | 15.384 | 1.00 | 77.59 |
| ATOM | 457 | C | GLU | 634 | 12.229 | 15.727 | 14.081 | 1.00 | 60.46 |

FIG. 5H

| | | | | | | | | |
|---|---|---|---|---|---|---|---|---|
| ATOM | 458 | O | GLU | 634 | 12.486 | 15.655 | 12.877 | 1.00 61.42 |
| ATOM | 459 | N | ILE | 635 | 12.783 | 14.913 | 14.993 | 1.00 59.27 |
| ATOM | 460 | H | ILE | 635 | 12.540 | 15.067 | 15.936 | 1.00 0.00 |
| ATOM | 461 | CA | ILE | 635 | 13.782 | 13.906 | 14.663 | 1.00 56.77 |
| ATOM | 462 | CB | ILE | 635 | 14.429 | 13.299 | 15.953 | 1.00 52.95 |
| ATOM | 463 | CG2 | ILE | 635 | 15.388 | 12.182 | 15.569 | 1.00 52.10 |
| ATOM | 464 | CG1 | ILE | 635 | 15.236 | 14.321 | 16.698 | 1.00 47.91 |
| ATOM | 465 | CD | ILE | 635 | 16.358 | 14.961 | 15.927 | 1.00 50.08 |
| ATOM | 466 | C | ILE | 635 | 13.110 | 12.816 | 13.854 | 1.00 57.26 |
| ATOM | 467 | O | ILE | 635 | 13.714 | 12.292 | 12.927 | 1.00 56.53 |
| ATOM | 468 | N | ASN | 636 | 11.854 | 12.452 | 14.086 | 1.00 58.11 |
| ATOM | 469 | H | ASN | 636 | 11.345 | 12.892 | 14.807 | 1.00 0.00 |
| ATOM | 470 | CA | ASN | 636 | 11.273 | 11.345 | 13.347 | 1.00 58.91 |
| ATOM | 471 | CB | ASN | 636 | 10.132 | 10.719 | 14.134 | 1.00 59.74 |
| ATOM | 472 | CG | ASN | 636 | 10.632 | 10.044 | 15.400 | 1.00 61.95 |
| ATOM | 473 | OD1 | ASN | 636 | 11.698 | 9.427 | 15.428 | 1.00 65.00 |
| ATOM | 474 | ND2 | ASN | 636 | 9.938 | 10.198 | 16.516 | 1.00 60.78 |
| ATOM | 475 | HD21 | ASN | 636 | 9.118 | 10.706 | 16.495 | 1.00 0.00 |
| ATOM | 476 | HD22 | ASN | 636 | 10.323 | 9.834 | 17.341 | 1.00 0.00 |
| ATOM | 477 | C | ASN | 636 | 10.775 | 11.849 | 12.030 | 1.00 59.34 |
| ATOM | 478 | O | ASN | 636 | 10.926 | 11.176 | 11.020 | 1.00 59.71 |
| ATOM | 479 | N | ASN | 637 | 10.278 | 13.076 | 12.015 | 1.00 59.84 |
| ATOM | 480 | H | ASN | 637 | 10.230 | 13.550 | 12.877 | 1.00 0.00 |
| ATOM | 481 | CA | ASN | 637 | 9.779 | 13.751 | 10.816 | 1.00 61.12 |
| ATOM | 482 | CB | ASN | 637 | 9.383 | 15.219 | 11.029 | 1.00 64.01 |
| ATOM | 483 | CG | ASN | 637 | 8.112 | 15.513 | 11.887 | 1.00 67.80 |
| ATOM | 484 | OD1 | ASN | 637 | 7.302 | 14.605 | 12.111 | 1.00 68.43 |
| ATOM | 485 | ND2 | ASN | 637 | 7.948 | 16.748 | 12.355 | 1.00 68.62 |
| ATOM | 486 | HD21 | ASN | 637 | 8.650 | 17.412 | 12.187 | 1.00 0.00 |
| ATOM | 487 | HD22 | ASN | 637 | 7.144 | 16.914 | 12.846 | 1.00 0.00 |
| ATOM | 488 | C | ASN | 637 | 10.834 | 13.839 | 9.723 | 1.00 61.25 |
| ATOM | 489 | O | ASN | 637 | 10.585 | 13.594 | 8.538 | 1.00 61.53 |
| ATOM | 490 | N | TYR | 638 | 12.033 | 14.300 | 10.102 | 1.00 60.30 |
| ATOM | 491 | H | TYR | 638 | 12.162 | 14.682 | 11.009 | 1.00 0.00 |
| ATOM | 492 | CA | TYR | 638 | 13.127 | 14.392 | 9.169 | 1.00 58.95 |
| ATOM | 493 | CB | TYR | 638 | 14.165 | 15.327 | 9.774 | 1.00 58.34 |
| ATOM | 494 | CG | TYR | 638 | 13.667 | 16.749 | 9.673 | 1.00 58.76 |
| ATOM | 495 | CD1 | TYR | 638 | 13.521 | 17.567 | 10.800 | 1.00 59.56 |
| ATOM | 496 | CE1 | TYR | 638 | 13.091 | 18.900 | 10.637 | 1.00 60.72 |
| ATOM | 497 | CD2 | TYR | 638 | 13.303 | 17.225 | 8.418 | 1.00 59.13 |
| ATOM | 498 | CE2 | TYR | 638 | 12.850 | 18.517 | 8.256 | 1.00 58.59 |
| ATOM | 499 | CZ | TYR | 638 | 12.738 | 19.343 | 9.354 | 1.00 59.43 |
| ATOM | 500 | OH | TYR | 638 | 12.451 | 20.666 | 9.088 | 1.00 58.81 |
| ATOM | 501 | HH | TYR | 638 | 12.351 | 20.876 | 8.165 | 1.00 0.00 |
| ATOM | 502 | C | TYR | 638 | 13.679 | 13.029 | 8.854 | 1.00 58.12 |
| ATOM | 503 | O | TYR | 638 | 14.008 | 12.788 | 7.698 | 1.00 58.25 |
| ATOM | 504 | N | THR | 639 | 13.706 | 12.108 | 9.796 | 1.00 57.10 |
| ATOM | 505 | H | THR | 639 | 13.402 | 12.348 | 10.690 | 1.00 0.00 |
| ATOM | 506 | CA | THR | 639 | 14.134 | 10.771 | 9.461 | 1.00 57.84 |
| ATOM | 507 | CB | THR | 639 | 14.163 | 9.904 | 10.683 | 1.00 57.69 |
| ATOM | 508 | OG1 | THR | 639 | 15.110 | 10.474 | 11.544 | 1.00 60.10 |
| ATOM | 509 | HG1 | THR | 639 | 14.818 | 11.323 | 11.889 | 1.00 0.00 |
| ATOM | 510 | CG2 | THR | 639 | 14.597 | 8.478 | 10.387 | 1.00 55.45 |
| ATOM | 511 | C | THR | 639 | 13.232 | 10.085 | 8.424 | 1.00 58.82 |
| ATOM | 512 | O | THR | 639 | 13.725 | 9.331 | 7.554 | 1.00 58.69 |
| ATOM | 513 | N | SER | 640 | 11.916 | 10.315 | 8.505 | 1.00 59.42 |
| ATOM | 514 | H | SER | 640 | 11.544 | 10.854 | 9.240 | 1.00 0.00 |
| ATOM | 515 | CA | SER | 640 | 10.997 | 9.745 | 7.531 | 1.00 60.07 |

FIG. 5I

| ATOM | 516 | CB | SER | 640 | 9.549 | 9.934 | 7.966 | 1.00 | 62.43 |
|------|-----|-----|-----|-----|--------|--------|--------|------|-------|
| ATOM | 517 | OG | SER | 640 | 9.343 | 9.238 | 9.188 | 1.00 | 69.53 |
| ATOM | 518 | HG | SER | 640 | 9.444 | 8.298 | 9.074 | 1.00 | 0.00 |
| ATOM | 519 | C | SER | 640 | 11.177 | 10.391 | 6.160 | 1.00 | 58.97 |
| ATOM | 520 | O | SER | 640 | 11.169 | 9.642 | 5.177 | 1.00 | 60.33 |
| ATOM | 521 | N | LEU | 641 | 11.375 | 11.710 | 6.057 | 1.00 | 56.88 |
| ATOM | 522 | H | LEU | 641 | 11.357 | 12.252 | 6.875 | 1.00 | 0.00 |
| ATOM | 523 | CA | LEU | 641 | 11.619 | 12.351 | 4.785 | 1.00 | 55.95 |
| ATOM | 524 | CB | LEU | 641 | 11.658 | 13.879 | 5.006 | 1.00 | 53.81 |
| ATOM | 525 | CG | LEU | 641 | 11.718 | 14.767 | 3.765 | 1.00 | 52.82 |
| ATOM | 526 | CD1 | LEU | 641 | 10.375 | 14.703 | 3.035 | 1.00 | 52.33 |
| ATOM | 527 | CD2 | LEU | 641 | 12.047 | 16.198 | 4.163 | 1.00 | 50.59 |
| ATOM | 528 | C | LEU | 641 | 12.948 | 11.832 | 4.190 | 1.00 | 56.33 |
| ATOM | 529 | O | LEU | 641 | 13.039 | 11.552 | 2.988 | 1.00 | 55.67 |
| ATOM | 530 | N | ILE | 642 | 13.988 | 11.612 | 5.019 | 1.00 | 55.99 |
| ATOM | 531 | H | ILE | 642 | 13.884 | 11.813 | 5.980 | 1.00 | 0.00 |
| ATOM | 532 | CA | ILE | 642 | 15.290 | 11.153 | 4.549 | 1.00 | 55.40 |
| ATOM | 533 | CB | ILE | 642 | 16.384 | 11.240 | 5.647 | 1.00 | 54.86 |
| ATOM | 534 | CG2 | ILE | 642 | 17.722 | 10.778 | 5.097 | 1.00 | 57.37 |
| ATOM | 535 | CG1 | ILE | 642 | 16.630 | 12.661 | 6.041 | 1.00 | 53.06 |
| ATOM | 536 | CD | ILE | 642 | 17.480 | 12.825 | 7.287 | 1.00 | 48.58 |
| ATOM | 537 | C | ILE | 642 | 15.163 | 9.729 | 4.112 | 1.00 | 55.08 |
| ATOM | 538 | O | ILE | 642 | 15.740 | 9.343 | 3.115 | 1.00 | 55.36 |
| ATOM | 539 | N | HIS | 643 | 14.415 | 8.904 | 4.785 | 1.00 | 55.14 |
| ATOM | 540 | H | HIS | 643 | 13.952 | 9.236 | 5.598 | 1.00 | 0.00 |
| ATOM | 541 | CA | HIS | 643 | 14.197 | 7.568 | 4.280 | 1.00 | 56.94 |
| ATOM | 542 | CB | HIS | 643 | 13.347 | 6.771 | 5.191 | 1.00 | 63.78 |
| ATOM | 543 | CG | HIS | 643 | 14.340 | 6.051 | 6.088 | 1.00 | 73.07 |
| ATOM | 544 | CD2 | HIS | 643 | 15.193 | 6.704 | 6.938 | 1.00 | 77.77 |
| ATOM | 545 | ND1 | HIS | 643 | 14.544 | 4.739 | 6.144 | 1.00 | 78.26 |
| ATOM | 546 | HD1 | HIS | 643 | 14.017 | 4.059 | 5.688 | 1.00 | 0.00 |
| ATOM | 547 | CE1 | HIS | 643 | 15.501 | 4.583 | 6.998 | 1.00 | 81.50 |
| ATOM | 548 | NE2 | HIS | 643 | 15.885 | 5.758 | 7.472 | 1.00 | 81.84 |
| ATOM | 549 | HE2 | HIS | 643 | 16.617 | 5.921 | 8.100 | 1.00 | 0.00 |
| ATOM | 550 | C | HIS | 643 | 13.527 | 7.512 | 2.940 | 1.00 | 55.82 |
| ATOM | 551 | O | HIS | 643 | 13.928 | 6.699 | 2.100 | 1.00 | 55.49 |
| ATOM | 552 | N | SER | 644 | 12.502 | 8.344 | 2.761 | 1.00 | 55.58 |
| ATOM | 553 | H | SER | 644 | 12.128 | 8.851 | 3.524 | 1.00 | 0.00 |
| ATOM | 554 | CA | SER | 644 | 11.826 | 8.384 | 1.478 | 1.00 | 54.97 |
| ATOM | 555 | CB | SER | 644 | 10.644 | 9.369 | 1.377 | 1.00 | 56.29 |
| ATOM | 556 | OG | SER | 644 | 9.823 | 9.759 | 2.572 | 1.00 | 59.92 |
| ATOM | 557 | HG | SER | 644 | 9.441 | 8.970 | 2.959 | 1.00 | 0.00 |
| ATOM | 558 | C | SER | 644 | 12.782 | 8.888 | 0.398 | 1.00 | 53.50 |
| ATOM | 559 | O | SER | 644 | 12.797 | 8.293 | -0.691 | 1.00 | 53.52 |
| ATOM | 560 | N | LEU | 645 | 13.612 | 9.918 | 0.673 | 1.00 | 51.33 |
| ATOM | 561 | H | LEU | 645 | 13.620 | 10.325 | 1.566 | 1.00 | 0.00 |
| ATOM | 562 | CA | LEU | 645 | 14.485 | 10.438 | -0.351 | 1.00 | 48.71 |
| ATOM | 563 | CB | LEU | 645 | 15.027 | 11.807 | 0.080 | 1.00 | 45.58 |
| ATOM | 564 | CG | LEU | 645 | 13.979 | 12.903 | 0.305 | 1.00 | 39.61 |
| ATOM | 565 | CD1 | LEU | 645 | 14.665 | 14.149 | 0.710 | 1.00 | 41.30 |
| ATOM | 566 | CD2 | LEU | 645 | 13.200 | 13.183 | -0.954 | 1.00 | 38.15 |
| ATOM | 567 | C | LEU | 645 | 15.593 | 9.476 | -0.651 | 1.00 | 48.35 |
| ATOM | 568 | O | LEU | 645 | 15.914 | 9.316 | -1.820 | 1.00 | 49.33 |
| ATOM | 569 | N | ILE | 646 | 16.114 | 8.734 | 0.334 | 1.00 | 48.24 |
| ATOM | 570 | H | ILE | 646 | 15.785 | 8.879 | 1.246 | 1.00 | 0.00 |
| ATOM | 571 | CA | ILE | 646 | 17.178 | 7.748 | 0.106 | 1.00 | 48.80 |
| ATOM | 572 | CB | ILE | 646 | 17.720 | 7.222 | 1.450 | 1.00 | 44.77 |
| ATOM | 573 | CG2 | ILE | 646 | 18.745 | 6.158 | 1.182 | 1.00 | 43.97 |

FIG. 5J

| | | | | | | | | |
|---|---|---|---|---|---|---|---|---|
| ATOM | 574 | CG1 | ILE | 646 | 18.414 | 8.325 | 2.218 | 1.00 43.19 |
| ATOM | 575 | CD | ILE | 646 | 18.854 | 7.897 | 3.621 | 1.00 39.46 |
| ATOM | 576 | C | ILE | 646 | 16.595 | 6.620 | -0.736 | 1.00 51.17 |
| ATOM | 577 | O | ILE | 646 | 17.236 | 6.140 | -1.676 | 1.00 50.43 |
| ATOM | 578 | N | GLU | 647 | 15.348 | 6.236 | -0.482 | 1.00 54.35 |
| ATOM | 579 | H | GLU | 647 | 14.843 | 6.711 | 0.208 | 1.00 0.00 |
| ATOM | 580 | CA | GLU | 647 | 14.685 | 5.186 | -1.244 | 1.00 56.99 |
| ATOM | 581 | CB | GLU | 647 | 13.408 | 4.828 | -0.527 | 1.00 62.05 |
| ATOM | 582 | CG | GLU | 647 | 12.691 | 3.564 | -1.047 | 1.00 71.88 |
| ATOM | 583 | CD | GLU | 647 | 11.372 | 3.218 | -0.346 | 1.00 79.96 |
| ATOM | 584 | OE1 | GLU | 647 | 10.947 | 3.931 | 0.578 | 1.00 83.26 |
| ATOM | 585 | OE2 | GLU | 647 | 10.766 | 2.217 | -0.738 | 1.00 83.60 |
| ATOM | 586 | C | GLU | 647 | 14.377 | 5.647 | -2.682 | 1.00 57.37 |
| ATOM | 587 | O | GLU | 647 | 14.604 | 4.923 | -3.662 | 1.00 58.06 |
| ATOM | 588 | N | GLU | 648 | 13.876 | 6.871 | -2.874 | 1.00 57.16 |
| ATOM | 589 | H | GLU | 648 | 13.711 | 7.409 | -2.074 | 1.00 0.00 |
| ATOM | 590 | CA | GLU | 648 | 13.588 | 7.431 | -4.178 | 1.00 57.13 |
| ATOM | 591 | CB | GLU | 648 | 13.051 | 8.796 | -4.039 | 1.00 62.05 |
| ATOM | 592 | CG | GLU | 648 | 12.503 | 9.437 | -5.318 | 1.00 74.11 |
| ATOM | 593 | CD | GLU | 648 | 11.969 | 10.872 | -5.126 | 1.00 85.94 |
| ATOM | 594 | OE1 | GLU | 648 | 11.991 | 11.409 | -4.008 | 1.00 91.79 |
| ATOM | 595 | OE2 | GLU | 648 | 11.521 | 11.471 | -6.110 | 1.00 88.20 |
| ATOM | 596 | C | GLU | 648 | 14.863 | 7.517 | -4.984 | 1.00 55.73 |
| ATOM | 597 | O | GLU | 648 | 14.864 | 7.188 | -6.175 | 1.00 55.55 |
| ATOM | 598 | N | SER | 649 | 15.950 | 7.961 | -4.364 | 1.00 54.84 |
| ATOM | 599 | H | SER | 649 | 15.881 | 8.274 | -3.436 | 1.00 0.00 |
| ATOM | 600 | CA | SER | 649 | 17.251 | 8.032 | -4.994 | 1.00 53.47 |
| ATOM | 601 | CB | SER | 649 | 18.191 | 8.704 | -4.055 | 1.00 52.08 |
| ATOM | 602 | OG | SER | 649 | 17.841 | 10.043 | -3.742 | 1.00 48.93 |
| ATOM | 603 | HG | SER | 649 | 17.888 | 10.547 | -4.561 | 1.00 0.00 |
| ATOM | 604 | C | SER | 649 | 17.811 | 6.694 | -5.403 | 1.00 52.80 |
| ATOM | 605 | O | SER | 649 | 18.368 | 6.564 | -6.482 | 1.00 53.07 |
| ATOM | 606 | N | GLN | 650 | 17.622 | 5.684 | -4.563 | 1.00 52.79 |
| ATOM | 607 | H | GLN | 650 | 17.260 | 5.899 | -3.670 | 1.00 0.00 |
| ATOM | 608 | CA | GLN | 650 | 17.985 | 4.285 | -4.808 | 1.00 53.64 |
| ATOM | 609 | CB | GLN | 650 | 17.547 | 3.387 | -3.634 | 1.00 56.65 |
| ATOM | 610 | CG | GLN | 650 | 18.565 | 2.745 | -2.685 | 1.00 62.17 |
| ATOM | 611 | CD | GLN | 650 | 17.982 | 2.264 | -1.334 | 1.00 66.78 |
| ATOM | 612 | OE1 | GLN | 650 | 16.991 | 1.535 | -1.224 | 1.00 69.78 |
| ATOM | 613 | NE2 | GLN | 650 | 18.538 | 2.637 | -0.192 | 1.00 67.82 |
| ATOM | 614 | HE21 | GLN | 650 | 19.324 | 3.204 | -0.193 | 1.00 0.00 |
| ATOM | 615 | HE22 | GLN | 650 | 18.083 | 2.295 | 0.609 | 1.00 0.00 |
| ATOM | 616 | C | GLN | 650 | 17.303 | 3.776 | -6.071 | 1.00 53.04 |
| ATOM | 617 | O | GLN | 650 | 17.951 | 3.085 | -6.882 | 1.00 54.05 |
| ATOM | 618 | N | ASN | 651 | 16.035 | 4.183 | -6.268 | 1.00 51.27 |
| ATOM | 619 | H | ASN | 651 | 15.627 | 4.783 | -5.608 | 1.00 0.00 |
| ATOM | 620 | CA | ASN | 651 | 15.261 | 3.761 | -7.435 | 1.00 49.91 |
| ATOM | 621 | CB | ASN | 651 | 13.776 | 4.018 | -7.246 | 1.00 49.79 |
| ATOM | 622 | CG | ASN | 651 | 13.276 | 3.154 | -6.125 | 1.00 53.41 |
| ATOM | 623 | OD1 | ASN | 651 | 13.709 | 2.010 | -5.961 | 1.00 52.64 |
| ATOM | 624 | ND2 | ASN | 651 | 12.418 | 3.728 | -5.276 | 1.00 59.61 |
| ATOM | 625 | HD21 | ASN | 651 | 12.157 | 4.647 | -5.399 | 1.00 0.00 |
| ATOM | 626 | HD22 | ASN | 651 | 12.154 | 3.212 | -4.475 | 1.00 0.00 |
| ATOM | 627 | C | ASN | 651 | 15.708 | 4.500 | -8.681 | 1.00 48.34 |
| ATOM | 628 | O | ASN | 651 | 15.988 | 3.912 | -9.726 | 1.00 47.51 |
| ATOM | 629 | N | GLN | 652 | 15.864 | 5.821 | -8.587 | 1.00 47.33 |
| ATOM | 630 | H | GLN | 652 | 15.598 | 6.247 | -7.749 | 1.00 0.00 |
| ATOM | 631 | CA | GLN | 652 | 16.350 | 6.623 | -9.690 | 1.00 47.23 |

FIG. 5K

| ATOM | 632 | CB | GLN | 652 | 16.307 | 8.040 | -9.279 | 1.00 | 45.56 |
|------|-----|------|-----|-----|--------|-------|---------|------|-------|
| ATOM | 633 | CG | GLN | 652 | 16.453 | 9.174 | -10.302 | 1.00 | 47.99 |
| ATOM | 634 | CD | GLN | 652 | 15.382 | 9.271 | -11.366 | 1.00 | 51.30 |
| ATOM | 635 | OE1 | GLN | 652 | 14.275 | 9.750 | -11.134 | 1.00 | 51.42 |
| ATOM | 636 | NE2 | GLN | 652 | 15.688 | 8.915 | -12.603 | 1.00 | 47.15 |
| ATOM | 637 | HE21 | GLN | 652 | 16.588 | 8.582 | -12.832 | 1.00 | 0.00 |
| ATOM | 638 | HE22 | GLN | 652 | 14.985 | 8.988 | -13.303 | 1.00 | 0.00 |
| ATOM | 639 | C | GLN | 652 | 17.758 | 6.187 | -10.002 | 1.00 | 47.47 |
| ATOM | 640 | O | GLN | 652 | 18.093 | 6.195 | -11.164 | 1.00 | 48.04 |
| ATOM | 641 | N | GLN | 653 | 18.596 | 5.741 | -9.080 | 1.00 | 47.45 |
| ATOM | 642 | H | GLN | 653 | 18.285 | 5.717 | -8.155 | 1.00 | 0.00 |
| ATOM | 643 | CA | GLN | 653 | 19.926 | 5.262 | -9.403 | 1.00 | 49.03 |
| ATOM | 644 | CB | GLN | 653 | 20.669 | 4.856 | -8.157 | 1.00 | 47.54 |
| ATOM | 645 | CG | GLN | 653 | 22.164 | 4.660 | -8.449 | 1.00 | 46.28 |
| ATOM | 646 | CD | GLN | 653 | 22.929 | 5.903 | -8.922 | 1.00 | 45.38 |
| ATOM | 647 | OE1 | GLN | 653 | 22.474 | 7.036 | -8.956 | 1.00 | 45.74 |
| ATOM | 648 | NE2 | GLN | 653 | 24.191 | 5.913 | -9.220 | 1.00 | 45.80 |
| ATOM | 649 | HE21 | GLN | 653 | 24.738 | 5.108 | -9.124 | 1.00 | 0.00 |
| ATOM | 650 | HE22 | GLN | 653 | 24.602 | 6.803 | -9.348 | 1.00 | 0.00 |
| ATOM | 651 | C | GLN | 653 | 19.851 | 4.058 | -10.322 | 1.00 | 51.89 |
| ATOM | 652 | O | GLN | 653 | 20.554 | 4.029 | -11.335 | 1.00 | 52.35 |
| ATOM | 653 | N | GLU | 654 | 18.952 | 3.102 | -10.025 | 1.00 | 54.43 |
| ATOM | 654 | H | GLU | 654 | 18.388 | 3.228 | -9.231 | 1.00 | 0.00 |
| ATOM | 655 | CA | GLU | 654 | 18.763 | 1.932 | -10.883 | 1.00 | 55.77 |
| ATOM | 656 | CB | GLU | 654 | 17.815 | 0.928 | -10.199 | 1.00 | 59.12 |
| ATOM | 657 | CG | GLU | 654 | 18.515 | 0.035 | -9.155 | 1.00 | 69.14 |
| ATOM | 658 | CD | GLU | 654 | 17.642 | -0.522 | -8.002 | 1.00 | 76.48 |
| ATOM | 659 | OE1 | GLU | 654 | 17.376 | -1.728 | -7.946 | 1.00 | 78.90 |
| ATOM | 660 | OE2 | GLU | 654 | 17.220 | 0.245 | -7.134 | 1.00 | 77.99 |
| ATOM | 661 | C | GLU | 654 | 18.222 | 2.339 | -12.253 | 1.00 | 55.11 |
| ATOM | 662 | O | GLU | 654 | 18.762 | 1.916 | -13.285 | 1.00 | 55.24 |
| ATOM | 663 | N | LYS | 655 | 17.219 | 3.226 | -12.313 | 1.00 | 54.37 |
| ATOM | 664 | H | LYS | 655 | 16.858 | 3.551 | -11.458 | 1.00 | 0.00 |
| ATOM | 665 | CA | LYS | 655 | 16.635 | 3.697 | -13.564 | 1.00 | 54.47 |
| ATOM | 666 | CB | LYS | 655 | 15.456 | 4.583 | -13.204 | 1.00 | 54.89 |
| ATOM | 667 | CG | LYS | 655 | 14.495 | 4.868 | -14.361 | 1.00 | 59.61 |
| ATOM | 668 | CD | LYS | 655 | 13.201 | 5.577 | -13.910 | 1.00 | 65.23 |
| ATOM | 669 | CE | LYS | 655 | 12.251 | 4.748 | -13.002 | 1.00 | 68.13 |
| ATOM | 670 | NZ | LYS | 655 | 10.937 | 5.360 | -12.806 | 1.00 | 69.83 |
| ATOM | 671 | HZ1 | LYS | 655 | 10.454 | 5.475 | -13.724 | 1.00 | 0.00 |
| ATOM | 672 | HZ2 | LYS | 655 | 11.029 | 6.298 | -12.366 | 1.00 | 0.00 |
| ATOM | 673 | HZ3 | LYS | 655 | 10.344 | 4.756 | -12.200 | 1.00 | 0.00 |
| ATOM | 674 | C | LYS | 655 | 17.643 | 4.441 | -14.445 | 1.00 | 54.88 |
| ATOM | 675 | O | LYS | 655 | 17.713 | 4.286 | -15.665 | 1.00 | 54.37 |
| ATOM | 676 | N | ASN | 656 | 18.474 | 5.275 | -13.838 | 1.00 | 56.18 |
| ATOM | 677 | H | ASN | 656 | 18.353 | 5.436 | -12.874 | 1.00 | 0.00 |
| ATOM | 678 | CA | ASN | 656 | 19.463 | 6.063 | -14.534 | 1.00 | 56.44 |
| ATOM | 679 | CB | ASN | 656 | 20.117 | 7.094 | -13.615 | 1.00 | 56.38 |
| ATOM | 680 | CG | ASN | 656 | 19.142 | 8.214 | -13.246 | 1.00 | 57.60 |
| ATOM | 681 | OD1 | ASN | 656 | 18.270 | 8.618 | -14.035 | 1.00 | 59.08 |
| ATOM | 682 | ND2 | ASN | 656 | 19.141 | 8.698 | -12.009 | 1.00 | 57.31 |
| ATOM | 683 | HD21 | ASN | 656 | 19.787 | 8.297 | -11.386 | 1.00 | 0.00 |
| ATOM | 684 | HD22 | ASN | 656 | 18.438 | 9.305 | -11.726 | 1.00 | 0.00 |
| ATOM | 685 | C | ASN | 656 | 20.510 | 5.128 | -15.026 | 1.00 | 57.72 |
| ATOM | 686 | O | ASN | 656 | 20.860 | 5.283 | -16.194 | 1.00 | 58.23 |
| ATOM | 687 | N | GLU | 657 | 20.960 | 4.129 | -14.248 | 1.00 | 58.95 |
| ATOM | 688 | H | GLU | 657 | 20.656 | 4.056 | -13.317 | 1.00 | 0.00 |
| ATOM | 689 | CA | GLU | 657 | 21.918 | 3.154 | -14.752 | 1.00 | 61.26 |

FIG. 5L

| | | | | | | | | |
|---|---|---|---|---|---|---|---|---|
| ATOM | 690 | CB | GLU | 657 | 22.297 | 2.184 | -13.687 | 1.00 62.42 |
| ATOM | 691 | CG | GLU | 657 | 23.051 | 2.811 | -12.514 | 1.00 65.99 |
| ATOM | 692 | CD | GLU | 657 | 23.410 | 1.852 | -11.389 | 1.00 68.51 |
| ATOM | 693 | OE1 | GLU | 657 | 23.152 | 0.650 | -11.481 | 1.00 72.44 |
| ATOM | 694 | OE2 | GLU | 657 | 23.970 | 2.322 | -10.407 | 1.00 69.49 |
| ATOM | 695 | C | GLU | 657 | 21.326 | 2.381 | -15.914 | 1.00 62.47 |
| ATOM | 696 | O | GLU | 657 | 21.999 | 2.178 | -16.920 | 1.00 62.52 |
| ATOM | 697 | N | GLN | 658 | 20.051 | 1.999 | -15.851 | 1.00 63.77 |
| ATOM | 698 | H | GLN | 658 | 19.527 | 2.154 | -15.036 | 1.00 0.00 |
| ATOM | 699 | CA | GLN | 658 | 19.379 | 1.342 | -16.972 | 1.00 64.97 |
| ATOM | 700 | CB | GLN | 658 | 17.908 | 1.040 | -16.710 | 1.00 67.79 |
| ATOM | 701 | CG | GLN | 658 | 17.473 | 0.109 | -15.580 | 1.00 69.56 |
| ATOM | 702 | CD | GLN | 658 | 15.981 | 0.184 | -15.253 | 1.00 71.90 |
| ATOM | 703 | OE1 | GLN | 658 | 15.214 | 1.130 | -15.491 | 1.00 69.19 |
| ATOM | 704 | NE2 | GLN | 658 | 15.580 | -0.892 | -14.597 | 1.00 73.46 |
| ATOM | 705 | HE21 | GLN | 658 | 16.241 | -1.579 | -14.383 | 1.00 0.00 |
| ATOM | 706 | HE22 | GLN | 658 | 14.637 | -0.917 | -14.331 | 1.00 0.00 |
| ATOM | 707 | C | GLN | 658 | 19.373 | 2.235 | -18.211 | 1.00 64.88 |
| ATOM | 708 | O | GLN | 658 | 19.620 | 1.701 | -19.282 | 1.00 64.89 |
| ATOM | 709 | N | GLU | 659 | 19.099 | 3.533 | -18.086 | 1.00 64.42 |
| ATOM | 710 | H | GLU | 659 | 18.930 | 3.898 | -17.190 | 1.00 0.00 |
| ATOM | 711 | CA | GLU | 659 | 19.001 | 4.408 | -19.239 | 1.00 64.32 |
| ATOM | 712 | CB | GLU | 659 | 18.413 | 5.726 | -18.809 | 1.00 68.95 |
| ATOM | 713 | CG | GLU | 659 | 18.001 | 6.640 | -19.976 | 1.00 78.11 |
| ATOM | 714 | CD | GLU | 659 | 17.379 | 7.956 | -19.530 | 1.00 86.51 |
| ATOM | 715 | OE1 | GLU | 659 | 17.214 | 8.159 | -18.321 | 1.00 90.49 |
| ATOM | 716 | OE2 | GLU | 659 | 17.049 | 8.781 | -20.388 | 1.00 90.41 |
| ATOM | 717 | C | GLU | 659 | 20.328 | 4.664 | -19.917 | 1.00 62.40 |
| ATOM | 718 | O | GLU | 659 | 20.389 | 5.040 | -21.080 | 1.00 61.69 |
| ATOM | 719 | N | LEU | 660 | 21.374 | 4.592 | -19.120 | 1.00 61.04 |
| ATOM | 720 | H | LEU | 660 | 21.231 | 4.584 | -18.144 | 1.00 0.00 |
| ATOM | 721 | CA | LEU | 660 | 22.691 | 4.691 | -19.683 | 1.00 60.69 |
| ATOM | 722 | CB | LEU | 660 | 23.697 | 4.805 | -18.521 | 1.00 60.36 |
| ATOM | 723 | CG | LEU | 660 | 24.642 | 6.019 | -18.618 | 1.00 59.86 |
| ATOM | 724 | CD1 | LEU | 660 | 23.883 | 7.314 | -18.999 | 1.00 64.42 |
| ATOM | 725 | CD2 | LEU | 660 | 25.334 | 6.131 | -17.317 | 1.00 55.37 |
| ATOM | 726 | C | LEU | 660 | 23.036 | 3.531 | -20.613 | 1.00 60.42 |
| ATOM | 727 | O | LEU | 660 | 23.705 | 3.774 | -21.615 | 1.00 60.27 |
| ATOM | 728 | N | LEU | 661 | 22.575 | 2.323 | -20.325 | 1.00 60.33 |
| ATOM | 729 | H | LEU | 661 | 21.881 | 2.223 | -19.630 | 1.00 0.00 |
| ATOM | 730 | CA | LEU | 661 | 22.856 | 1.140 | -21.141 | 1.00 60.95 |
| ATOM | 731 | CB | LEU | 661 | 22.646 | -0.115 | -20.264 | 1.00 59.85 |
| ATOM | 732 | CG | LEU | 661 | 23.452 | -0.260 | -18.988 | 1.00 57.97 |
| ATOM | 733 | CD1 | LEU | 661 | 23.106 | -1.535 | -18.261 | 1.00 57.79 |
| ATOM | 734 | CD2 | LEU | 661 | 24.896 | -0.304 | -19.360 | 1.00 54.71 |
| ATOM | 735 | C | LEU | 661 | 22.049 | 0.974 | -22.446 | 1.00 61.99 |
| ATOM | 736 | OT1 | LEU | 661 | 20.871 | 1.318 | -22.502 | 1.00 60.13 |
| ATOM | 737 | OT2 | LEU | 661 | 22.634 | 0.490 | -23.411 | 1.00 64.98 |
| ATOM | 738 | OH2 | HOH | 130 | 20.374 | 11.213 | -18.121 | 1.00 71.66 |
| ATOM | 739 | H1 | HOH | 130 | 20.431 | 10.325 | -18.535 | 1.00 0.00 |
| ATOM | 740 | H2 | HOH | 130 | 19.472 | 11.248 | -17.822 | 1.00 0.00 |
| ATOM | 741 | OH2 | HOH | 131 | 21.271 | 8.706 | -17.797 | 1.00 41.79 |
| ATOM | 742 | H1 | HOH | 131 | 21.310 | 7.838 | -17.376 | 1.00 0.00 |
| ATOM | 743 | H2 | HOH | 131 | 22.207 | 8.971 | -17.787 | 1.00 0.00 |
| ATOM | 744 | OH2 | HOH | 132 | 20.650 | 1.729 | -6.022 | 1.00 46.90 |
| ATOM | 745 | H1 | HOH | 132 | 19.744 | 1.986 | -6.245 | 1.00 0.00 |
| ATOM | 746 | H2 | HOH | 132 | 21.074 | 2.571 | -5.777 | 1.00 0.00 |
| ATOM | 747 | OH2 | HOH | 133 | 22.303 | 1.121 | -8.408 | 1.00 60.62 |

FIG. 5M

| | | | | | | | | |
|---|---|---|---|---|---|---|---|---|
| ATOM | 748 | H1 | HOH | 133 | 22.825 | 1.923 | -8.306 | 1.00 0.00 |
| ATOM | 749 | H2 | HOH | 133 | 21.811 | 1.091 | -7.565 | 1.00 0.00 |
| ATOM | 750 | OH2 | HOH | 134 | 12.657 | 5.253 | 8.200 | 1.00 56.12 |
| ATOM | 751 | H1 | HOH | 134 | 12.382 | 4.344 | 8.353 | 1.00 0.00 |
| ATOM | 752 | H2 | HOH | 134 | 11.869 | 5.752 | 8.457 | 1.00 0.00 |
| ATOM | 753 | OH2 | HOH | 135 | 9.078 | 18.813 | 26.094 | 1.00 49.33 |
| ATOM | 754 | H1 | HOH | 135 | 9.131 | 17.970 | 25.664 | 1.00 0.00 |
| ATOM | 755 | H2 | HOH | 135 | 9.244 | 19.463 | 25.419 | 1.00 0.00 |
| ATOM | 756 | OH2 | HOH | 136 | 7.670 | 21.185 | 11.788 | 1.00 53.95 |
| ATOM | 757 | H1 | HOH | 136 | 7.025 | 21.036 | 12.470 | 1.00 0.00 |
| ATOM | 758 | H2 | HOH | 136 | 8.510 | 21.265 | 12.230 | 1.00 0.00 |
| ATOM | 759 | OH2 | HOH | 137 | 8.303 | 19.620 | 23.607 | 1.00 92.51 |
| ATOM | 760 | H1 | HOH | 137 | 8.399 | 18.988 | 22.917 | 1.00 0.00 |
| ATOM | 761 | H2 | HOH | 137 | 9.047 | 20.193 | 23.630 | 1.00 0.00 |
| ATOM | 762 | OH2 | HOH | 138 | 14.426 | 18.177 | 16.971 | 1.00 91.64 |
| ATOM | 763 | H1 | HOH | 138 | 15.010 | 18.890 | 16.831 | 1.00 0.00 |
| ATOM | 764 | H2 | HOH | 138 | 13.573 | 18.570 | 17.105 | 1.00 0.00 |
| ATOM | 765 | OH2 | HOH | 139 | 6.660 | 18.291 | 14.901 | 1.00 47.78 |
| ATOM | 766 | H1 | HOH | 139 | 6.912 | 18.615 | 14.042 | 1.00 0.00 |
| ATOM | 767 | H2 | HOH | 139 | 7.036 | 18.893 | 15.527 | 1.00 0.00 |
| ATOM | 768 | OH2 | HOH | 140 | 9.801 | 17.869 | 7.746 | 1.00 50.95 |
| ATOM | 769 | H1 | HOH | 140 | 9.411 | 16.994 | 7.627 | 1.00 0.00 |
| ATOM | 770 | H2 | HOH | 140 | 10.574 | 17.739 | 8.259 | 1.00 0.00 |
| ATOM | 771 | OH2 | HOH | 141 | 7.790 | 15.753 | 8.005 | 1.00 53.41 |
| ATOM | 772 | H1 | HOH | 141 | 7.613 | 15.541 | 8.927 | 1.00 0.00 |
| ATOM | 773 | H2 | HOH | 141 | 8.562 | 15.235 | 7.778 | 1.00 0.00 |
| ATOM | 774 | OH2 | HOH | 142 | 14.145 | 18.206 | 2.097 | 1.00 57.88 |
| ATOM | 775 | H1 | HOH | 142 | 14.620 | 17.400 | 2.308 | 1.00 0.00 |
| ATOM | 776 | H2 | HOH | 142 | 13.290 | 18.116 | 2.522 | 1.00 0.00 |
| ATOM | 777 | OH2 | HOH | 143 | 12.314 | 6.447 | -8.867 | 1.00 65.60 |
| ATOM | 778 | H1 | HOH | 143 | 12.737 | 7.223 | -9.273 | 1.00 0.00 |
| ATOM | 779 | H2 | HOH | 143 | 12.746 | 6.378 | -8.026 | 1.00 0.00 |
| ATOM | 780 | OH2 | HOH | 144 | 21.545 | -1.804 | -13.790 | 1.00 49.07 |
| ATOM | 781 | H1 | HOH | 144 | 21.496 | -2.647 | -14.243 | 1.00 0.00 |
| ATOM | 782 | H2 | HOH | 144 | 20.714 | -1.364 | -13.979 | 1.00 0.00 |
| ATOM | 783 | OH2 | HOH | 145 | 22.569 | 8.158 | -11.409 | 1.00 46.71 |
| ATOM | 784 | H1 | HOH | 145 | 22.403 | 7.556 | -10.690 | 1.00 0.00 |
| ATOM | 785 | H2 | HOH | 145 | 22.970 | 8.920 | -10.966 | 1.00 0.00 |
| ATOM | 786 | OH2 | HOH | 146 | 15.788 | 9.728 | -7.160 | 1.00 65.57 |
| ATOM | 787 | H1 | HOH | 146 | 16.729 | 9.881 | -7.059 | 1.00 0.00 |
| ATOM | 788 | H2 | HOH | 146 | 15.600 | 8.894 | -6.726 | 1.00 0.00 |
| ATOM | 789 | OH2 | HOH | 147 | 7.205 | 11.385 | 12.307 | 1.00 55.74 |
| ATOM | 790 | H1 | HOH | 147 | 8.081 | 11.402 | 11.900 | 1.00 0.00 |
| ATOM | 791 | H2 | HOH | 147 | 6.937 | 12.318 | 12.282 | 1.00 0.00 |
| ATOM | 792 | OH2 | HOH | 148 | 9.847 | 10.295 | -2.390 | 1.00 38.62 |
| ATOM | 793 | H1 | HOH | 148 | 8.917 | 10.375 | -2.193 | 1.00 0.00 |
| ATOM | 794 | H2 | HOH | 148 | 10.216 | 9.724 | -1.732 | 1.00 0.00 |
| ATOM | 795 | OH2 | HOH | 149 | 14.009 | 23.313 | 28.896 | 1.00 73.77 |
| ATOM | 796 | H1 | HOH | 149 | 14.838 | 23.163 | 28.435 | 1.00 0.00 |
| ATOM | 797 | H2 | HOH | 149 | 13.892 | 22.574 | 29.472 | 1.00 0.00 |
| ATOM | 798 | OH2 | HOH | 150 | 13.472 | 10.407 | -8.621 | 1.00 45.61 |
| ATOM | 799 | H1 | HOH | 150 | 13.745 | 10.082 | -9.473 | 1.00 0.00 |
| ATOM | 800 | H2 | HOH | 150 | 14.142 | 10.063 | -8.014 | 1.00 0.00 |
| ATOM | 801 | OH2 | HOH | 151 | 11.244 | 11.155 | -10.623 | 1.00 56.60 |
| ATOM | 802 | H1 | HOH | 151 | 10.350 | 11.480 | -10.481 | 1.00 0.00 |
| ATOM | 803 | H2 | HOH | 151 | 11.708 | 11.979 | -10.633 | 1.00 0.00 |
| ATOM | 804 | OH2 | HOH | 152 | 4.167 | 17.232 | 14.430 | 1.00 59.26 |
| ATOM | 805 | H1 | HOH | 152 | 3.234 | 17.266 | 14.255 | 1.00 0.00 |

FIG. 5N

| | | | | | | | | | |
|---|---|---|---|---|---|---|---|---|---|
| ATOM | 806 | H2 | HOH | 152 | 4.325 | 17.835 | 15.160 | 1.00 | 0.00 |
| ATOM | 807 | OH2 | HOH | 153 | 7.289 | 13.019 | 7.362 | 1.00 | 59.36 |
| ATOM | 808 | H1 | HOH | 153 | 6.985 | 13.870 | 7.006 | 1.00 | 0.00 |
| ATOM | 809 | H2 | HOH | 153 | 6.571 | 12.413 | 7.174 | 1.00 | 0.00 |
| ATOM | 810 | OH2 | HOH | 154 | 7.898 | 10.616 | 4.187 | 1.00 | 53.34 |
| ATOM | 811 | H1 | HOH | 154 | 8.656 | 10.430 | 4.750 | 1.00 | 0.00 |
| ATOM | 812 | H2 | HOH | 154 | 8.245 | 10.424 | 3.311 | 1.00 | 0.00 |
| ATOM | 813 | OH2 | HOH | 155 | 18.700 | 5.086 | 6.487 | 1.00 | 58.77 |
| ATOM | 814 | H1 | HOH | 155 | 19.339 | 4.385 | 6.621 | 1.00 | 0.00 |
| ATOM | 815 | H2 | HOH | 155 | 18.262 | 5.154 | 7.320 | 1.00 | 0.00 |
| ATOM | 816 | OH2 | HOH | 156 | 14.706 | 8.287 | -15.323 | 1.00 | 71.36 |
| ATOM | 817 | H1 | HOH | 156 | 13.983 | 8.106 | -15.937 | 1.00 | 0.00 |
| ATOM | 818 | H2 | HOH | 156 | 15.493 | 8.205 | -15.863 | 1.00 | 0.00 |
| ATOM | 819 | OH2 | HOH | 157 | 17.583 | 10.761 | -18.187 | 1.00 | 49.62 |
| ATOM | 820 | H1 | HOH | 157 | 17.448 | 10.166 | -18.942 | 1.00 | 0.00 |
| ATOM | 821 | H2 | HOH | 157 | 17.684 | 10.091 | -17.473 | 1.00 | 0.00 |
| ATOM | 822 | OH2 | HOH | 158 | 16.849 | 14.385 | -20.221 | 1.00 | 59.72 |
| ATOM | 823 | H1 | HOH | 158 | 16.623 | 13.960 | -19.443 | 1.00 | 0.00 |
| ATOM | 824 | H2 | HOH | 158 | 16.025 | 14.098 | -20.716 | 1.00 | 0.00 |
| ATOM | 825 | OH2 | HOH | 159 | 23.359 | 25.370 | 14.837 | 1.00 | 57.74 |
| ATOM | 826 | H1 | HOH | 159 | 23.884 | 26.063 | 14.430 | 1.00 | 0.00 |
| ATOM | 827 | H2 | HOH | 159 | 23.387 | 25.608 | 15.758 | 1.00 | 0.00 |
| ATOM | 828 | OH2 | HOH | 160 | 17.498 | 22.874 | 16.925 | 1.00 | 93.45 |
| ATOM | 829 | H1 | HOH | 160 | 17.242 | 23.753 | 16.701 | 1.00 | 0.00 |
| ATOM | 830 | H2 | HOH | 160 | 16.839 | 22.592 | 17.567 | 1.00 | 0.00 |
| ATOM | 831 | OH2 | HOH | 161 | 20.348 | 23.693 | 23.117 | 1.00 | 63.40 |
| ATOM | 832 | H1 | HOH | 161 | 21.038 | 23.780 | 23.785 | 1.00 | 0.00 |
| ATOM | 833 | H2 | HOH | 161 | 20.407 | 22.764 | 22.840 | 1.00 | 0.00 |
| ATOM | 834 | OH2 | HOH | 162 | 26.302 | 25.733 | 28.760 | 1.00 | 74.83 |
| ATOM | 835 | H1 | HOH | 162 | 26.307 | 26.586 | 28.361 | 1.00 | 0.00 |
| ATOM | 836 | H2 | HOH | 162 | 25.982 | 25.835 | 29.661 | 1.00 | 0.00 |
| ATOM | 837 | OH2 | HOH | 163 | 25.950 | 24.779 | 25.047 | 1.00 | 73.62 |
| ATOM | 838 | H1 | HOH | 163 | 26.734 | 24.588 | 25.612 | 1.00 | 0.00 |
| ATOM | 839 | H2 | HOH | 163 | 26.332 | 25.366 | 24.401 | 1.00 | 0.00 |
| ATOM | 840 | OH2 | HOH | 164 | 11.696 | 17.842 | 0.575 | 1.00 | 63.54 |
| ATOM | 841 | H1 | HOH | 164 | 12.559 | 17.505 | 0.750 | 1.00 | 0.00 |
| ATOM | 842 | H2 | HOH | 164 | 11.078 | 17.126 | 0.562 | 1.00 | 0.00 |
| ATOM | 843 | OH2 | HOH | 165 | 14.262 | 19.203 | 4.844 | 1.00 | 48.44 |
| ATOM | 844 | H1 | HOH | 165 | 13.591 | 19.435 | 5.469 | 1.00 | 0.00 |
| ATOM | 845 | H2 | HOH | 165 | 15.124 | 19.290 | 5.226 | 1.00 | 0.00 |
| ATOM | 846 | OH2 | HOH | 166 | 15.984 | 22.052 | -2.490 | 1.00 | 62.80 |
| ATOM | 847 | H1 | HOH | 166 | 15.327 | 21.946 | -3.200 | 1.00 | 0.00 |
| ATOM | 848 | H2 | HOH | 166 | 15.529 | 21.751 | -1.706 | 1.00 | 0.00 |
| ATOM | 849 | OH2 | HOH | 167 | 16.135 | 20.908 | -5.213 | 1.00 | 82.35 |
| ATOM | 850 | H1 | HOH | 167 | 16.482 | 20.062 | -4.835 | 1.00 | 0.00 |
| ATOM | 851 | H2 | HOH | 167 | 15.378 | 20.538 | -5.665 | 1.00 | 0.00 |
| ATOM | 852 | OH2 | HOH | 168 | 10.937 | 6.573 | -6.161 | 1.00 | 63.06 |
| ATOM | 853 | H1 | HOH | 168 | 11.244 | 5.996 | -5.478 | 1.00 | 0.00 |
| ATOM | 854 | H2 | HOH | 168 | 11.691 | 7.003 | -6.564 | 1.00 | 0.00 |
| ATOM | 855 | OH2 | HOH | 169 | 9.077 | 12.911 | -2.911 | 1.00 | 64.88 |
| ATOM | 856 | H1 | HOH | 169 | 8.184 | 13.199 | -3.064 | 1.00 | 0.00 |
| ATOM | 857 | H2 | HOH | 169 | 9.394 | 12.597 | -3.765 | 1.00 | 0.00 |
| ATOM | 858 | OH2 | HOH | 170 | 13.272 | 7.391 | 13.889 | 1.00 | 65.83 |
| ATOM | 859 | H1 | HOH | 170 | 13.766 | 6.842 | 13.286 | 1.00 | 0.00 |
| ATOM | 860 | H2 | HOH | 170 | 13.421 | 8.306 | 13.606 | 1.00 | 0.00 |
| ATOM | 861 | OH2 | HOH | 171 | 6.871 | 10.837 | 16.390 | 1.00 | 58.39 |
| ATOM | 862 | H1 | HOH | 171 | 6.258 | 11.055 | 15.679 | 1.00 | 0.00 |
| ATOM | 863 | H2 | HOH | 171 | 7.611 | 11.410 | 16.223 | 1.00 | 0.00 |

FIG. 50

```
ATOM   864  OH2  HOH   172      14.184   12.148   23.463   1.00  73.66
ATOM   865  H1   HOH   172      14.543   11.552   22.797   1.00   0.00
ATOM   866  H2   HOH   172      13.316   12.368   23.168   1.00   0.00
END
```

CORE STRUCTURE OF GP41 FROM THE HIV ENVELOPE GLYCOPROTEIN

RELATED APPLICATION(S)

This application is a Divisional Application of Ser. No. 09/062,241, now U.S. Pat. No. 6,150,088, entitled, "Core Structure of gp41 From the HIV Envelope Glycoprotein", by David C. Chan, Deborah Fass, Min Lu, James M. Berger and Peter S. Kim, (filed on Apr. 17, 1998) which claims the benefit of U.S. Provisional Application No. 60/043,280, entitled "Core Structure of gp41 from the HIV Envelope Glycoprotein", by David C. Chan, Deborah Fass, Min Lu, James M. Berger and Peter S. Kim (filed Apr. 17, 1997). The entire teachings of U.S. application Ser. No. 09/062,241 and U.S. Provisional Application No. 60/043,280 are expressly incorporated herein by reference.

GOVERNMENT SUPPORT

Work described herein was funded by the Howard Hughes Medical Institute.

BACKGROUND OF THE INVENTION

The surface glycoproteins of enveloped viruses play critical roles in the initial events of viral infection, mediating virion attachment to cells and fusion of the viral and immune response in infected hosts. Envelope glycoproteins are also major targets for the anti-viral immune response in infected hosts. The human immunodeficiency virus type 1 (HIV-1) envelope glycoprotein consists of two noncovalently associated subunits, gp120 and gp41, that are generated by proteolytic cleavage of a precursor polypeptide, gp160. Luciw, P. A., In *Fields Virology,* Third Edition, B. N. Fields et al., eds., Lippincott-Raven Publishers, Philadelphia, pp. 1881–1952 (1996); Freed, E. O. et al., *J. Biol. Chem.* 270: 23883–23886 (1995). gp120 directs target-cell recognition and viral tropism through interaction with the cell-surface receptor CD4 and one of several co-receptors that are members of the chemokine receptor family. Broder, C. C. et al., *Pathobiology* 64:171–179 (1996); D'Souza, M. P. et al., *Nature Med.* 2:1293–1300 (1996); Wilkinson, D., *Current Biology* 6:1051–1053 (1996). The membrane-spanning gp41 subunit then promotes fusion of the viral and cellular membranes, a process that results in the release of viral contents into the host cell. It has not yet been possible to obtain a detailed structure for gp41, either alone or in complex with gp120.

SUMMARY OF THE INVENTION

Described herein is the crystal structure of the α-helical domain of the gp41 component of HIV-1 envelope glycoprotein which represents the core of fusion-active gp41. Also described herein is Applicants' determination, with reference to the crystal structure, that certain amino acid residues within the core are essential for interaction of the component peptides and, thus, for gp41 activity. The core of fusion-active gp41 is composed of a trimer of two interacting peptides, referred to here as N36 and C34. The minimal stable envelope subdomain has been shown to consist of a 36-residue peptide (N-36) and a 34-residue peptide (C-34) whose amino acid sequences are presented below. The crystal structure of the N36/C34 complex is a six-helix bundle in which three N36 helices form an interior, parallel coiled coil and three C34 helices pack in an oblique, anti-parallel manner into highly conserved, hydrophobic grooves on the surface of the N36 trimer. It shows striking similarity to the low-pH induced conformation of influenza hemagglutinin (HA).

Applicants have determined the structural basis for interaction between two peptide fragments of HIV gp41: one peptide fragment derived from the N-terminal region of the ectodomain of gp41 and one peptide fragment derived from the C-terminal region of the gp41 ectodomain. The N-terminal peptide fragment, N36, includes amino acid residue 546 through and including amino acid residue 581, numbered according to their position in HIV-1 gp160; it includes amino acid residues which comprise a region of the ectodomain which encompasses the 4-3 hydrophobic repeat. The amino acid sequence of the N36 peptide is:
SGIVQQQNNLLRAIEAQQHLLQLTVWGIKQLQARIL (SEQ ID NO.: 1).
The C-terminal region peptide fragment C34 includes amino acid residue 628 through and including amino acid residue 661, numbered according to their position in HIV-1 gp160; it is derived from the region prior to the transmembrane segment. The amino acid sequence of the C34 peptide is:
WMEWDREINNYTSLIHSLIEESQNQQEKNEQELL (SEQ ID NO.: 2). The three-dimension coordinates for the atoms in the N36/C34 gp41 complex are presented herein. They can be used to display the structure of the complex and to design molecules (drugs) which interact with gp41 and inhibit its activity, such as those which prevent interaction of key components (amino acid residues) of the α-helical domain which represents the core of fusion-active gp41.

Work described herein provides, for the first time, an understanding of how the N-terminal peptide and the C-terminal peptide interact. The crystal structure and information regarding the interactions of these two peptides provide the basis for development of drugs which inhibit HIV infection, such as peptidomimetic or small-molecule inhibitors, using such methods as combinatorial chemistry or rational drug design. Drugs developed or identified with reference to the information provided herein are also the subject of the present invention. Drugs which fit into or line the N-peptide cavity, prevent the N-peptide cavity from accommodating amino acid residues or peptides from the C-terminal region of gp41 and, thus, prevent or inhibit gp41 activity are the subject of this invention. Such drugs can be identified with reference to the information about the structure of the complex and the cavity shown to be present in the N36 trimer, provided herein, or with reference to information about the structure of the complex and the three dimensional coordinates of the cavity, also provided herein, and known methods. In a particular embodiment of identifying or designing a molecule which inhibits the fusion active form of gp41 and, thus, inhibit HIV, in which combinatorial chemistry is used, a library biased to include an increased number of indole rings, hydrophobic moieties and/or negatively charged molecules is used. An antibody which binds these key areas of fusion-active gp41 is also the subject of the invention. For example, an immunogen which is or includes a molecule with the coordinates described herein or the N-peptide core can be used to immunize an individual, resulting in production of antibodies that bind the cavity or pocket on the N-terminal peptide and, thus, render it unavailable for its normal interactions and prevent or inhibit gp41 activity.

BRIEF DESCRIPTION OF THE DRAWINGS

The patent or application file contains at least one drawing executed in color. Copies of this patent or patent application publication with color drawings will be provided by the Office upon request and payment of the necessary fee.

FIG. 3A shows an end-on view of the N36/C34 complex looking down the three-fold axis of the trimer. FIG. 3B shows a side view with one N36 and one C34 helix labeled. The amino termini of the N36 helices (grey) point towards the top of the page, while those of the C34 helices (black) point towards the bottom. Diagrams were prepared using the program MOLSCRIPT (Kraulis, P., *J. Appl. Cryst.* 24:924–950 (1991)).

FIGS. 5A–5P present the three-dimension coordinates for the atoms in the N36/C34 gp41 complex; the atom types (column 3) in each amino acid (column 4) are listed, along with their coordinates (columns 6, 7, 8) in space. The three-dimension coordinates can be used to display the structure of the N36/C34 complex. The coordinates are available from the Protein Data Bank at the Brookhaven National Laboratory.

DETAILED DESCRIPTION OF THE INVENTION

Figure 1:
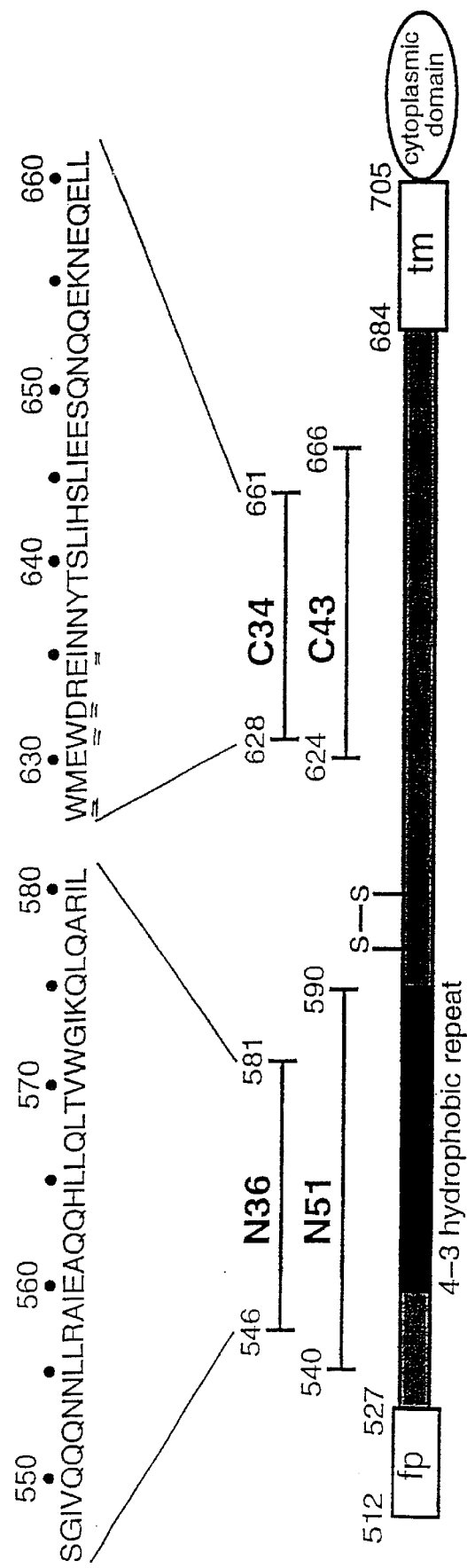
FIG. 1 is a schematic view of gp41 showing important functional regions, including the 4-3 hydrophobic repeat, the fusion peptide (fp), a disulfide linkage (S—S), and the transmembrane region (tm). The ectodomain is drawn approximately to scale. The peptides identified by protein dissection are shown above, along with the sequences of N36 and C34. The residues are numbered according to their position in gp160.

For the first time, a high-resolution picture of the protein fragment that enables HIV to invade human cells has been produced. As described, Applicants have determined the crystal structure of a key fragment of the HIV envelope protein. The envelope protein resides on the surface of the virus and plays a crucial role in HIV infection. One part of the protein, known as gp120, allows the virus to bind to human cells. Another subunit, gp41, mediates fusion of the viral membrane and the cell membrane—it initiates entry of the virus into the cell. The core structure of gp41 has been determined using X-ray crystallography.

The images of the protein fragment reveal a compact, six-helix bundle punctuated by deep cavities which are key targets for the development of new antiviral drugs. The existence of the cavities could not have been determined without the images.

Despite its importance, there are no antiviral drugs that target the envelope protein of HIV, in part because the virus is extraordinarily clever at changing the pieces of the protein it presents to the outside world. Work presented herein shows that the cavity structure may not be so amenable to change; therefore, drugs directed towards this region are useful against many HIV strains.

The HIV fusion protein has characteristics similar to those of the fusion structure of influenza virus. Surprisingly, the HIV fusion protein has a deep cavity or pocket at the base of each groove in the N36 coiled coil. In the active structure, each cavity is filled by a knob-like protrusion from C34. This ball-and-socket arrangement of C34 and N36 is a target for drug design or discovery. The structure, combined with data from other laboratories, supports the idea that a small molecule constructed specifically to block this interaction will stop fusion and prevent the virus from entering cells.

There are at least three reasons why such a molecule would be effective in preventing HIV from entering cells. First, test tube studies have shown that fragments, or peptides, of gp41 encompassing or overlapping with N36 or C34 have potent anti-viral activity. However, peptides generally make poor drugs because they are poorly absorbed and the body breaks them down almost immediately. A small molecule targeting just the cavity structure could escape this fate.

Second, the inhibitors derived from the C and N peptides are effective in the test tube against a wide range of HIV strains, including patient isolates and laboratory-adapted strains. By contrast, neutralizing antibodies and drug candidates designed to block the binding activity of the envelope protein are typically effective against only a limited subset of HIV strains.

Third, alteration of the walls of the N36 cavity can block the fusion reaction, indicating that the ball-and-socket arrangement of N36 and C34 must be preserved to obtain viral infection. In addition, the protein building blocks that make up the walls are highly conserved among HIV strains and between HIV and SIV, the virus responsible for AIDS in monkeys. This suggests that the virus cannot tolerate much change in this region and that HIV may have more difficulty developing resistance to a cavity-blocking drug than to many other compounds.

Applicants have analyzed the crystal structure of the α-helical domain of the HIV-1 transmembrane protein gp41 by means of assessment of a complex, referred to herein as the N36/C34 complex, which is composed of two interacting peptides: N36, which is derived from the N-terminal region of the gp41 ectodomain and C34, which is derived from the C-terminal region of the gp41 ectodomain. As described herein, Applicants have shown that the N36/C34 complex is a six-helix bundle (FIG. 3), in which the center consists of a parallel, trimeric coiled-coil of three N36 helices wrapped in a gradual left-handed superhelix. Three C34 helices wrap antiparallel to the N36 helices in a left-handed direction around the outside of the central coiled-coil N36 trimer. The N36/C34 complex is a cylinder which is approximately 35 Å in diameter and approximately 55 Å in height. FIG. 4 is a helical wheel representations of N36 and C34 in which three N36 helices and one C34 helix are represented as helical wheel projections. As can be seen, the interior amino acid residues at the a and d positions of the N36 heptad repeat are predominately hydrophobic (isoleucine, leucine). The characteristic "knobs-into-holes" packing of coiled coils occurs in the N36 trimer. That is, the amino acid residues (knobs) at the a and d layers pack into cavities (holes) between four residues of an adjacent helix. Crick, F. H. C., *Acta. Cryst.*, 6: 689–697 (1953); O'Shea, E. K., et al., *Science*, 254:539–544 (1991). Further description of the N36 trimer is presented in Example 2.

An electrostatic potential map of the cylindrical N36 superhelix shows that the surface of the superhelix is largely uncharged. The grooves that are the sites for C34 interaction have been determined to be lined with predominantly hydrophobic amino acid residues. The surface of the N36/C34 complex is much more highly charged than the isolated N-peptides, due to the acidic residues on the outside of the C34 helices. This explains why the heterodimeric complex exhibits greater solubility than the isolated peptides.

Three C34 helices pack obliquely against the outside of the N36 coiled-coil trimer in an antiparallel orientation. Interaction between the C34 helices and N36 occurs mainly through hydrophobic residues in three grooves on the surface of the central coiled-coil trimer. The amino acid residues which line these grooves are highly conserved between HIV and SIV gp41. In contrast, the N36 residues which flank the C34 helices are divergent. The pattern of sequence conservation is also apparent on the helical wheel representation of three N36 helices and one C34 helix of FIG. 4. (See Example 3.)

Each of the grooves on the surface of the N36 trimer has a particularly deep cavity. The cavity is approximately 16 Å long, approximately 7 Å wide and approximately 5–6 Å deep. It accommodates three hydrophobic amino acid residues from the abutting C34 helix: isoleucine-635($I_{635}$), tryptophan-631 ($W_{631}$) and tryptophan-628 ($W_{628}$). The top of the N36 cavity is lined by leucine-566 (Leu-566) of the left N36 helix and leucine-565 (Leu-565) of the right N36 helix. The left side of the cavity is formed by side chains from the left N36 helix, including amino acid residues (top to bottom): valine-570 (Val-570), lysine-574 (Lys-574, aliphatic portion) and glutamine-577 (Gln-577). The right wall of the cavity is formed by amino acid residues leucine-568 (Leu-568), tryptophan-571 (Trp-571) and glycine-572 (Gly-572) of the right N36 helix. The cavity floor is composed of threonine-569 (Thr-569), isoleucine-573 (Ile-573) and leucine-576 (Leu-576). Thus, interactions within the cavity are predominantly hydrophobic. In addition, aspartic acid-632 (Asp-632) of C34 forms a conserved salt bridge with lysine-574 (Lys-574) of N36 immediately to the left of the cavity.

As a result of the work described, a region of the HIV-1 transmembrane protein gp41 which is a target for HIV inhibitors has been defined and is available for designing and/or developing new drugs and identifying existing drugs which inhibit HIV. A particularly valuable target for an HIV inhibitor are the highly conserved, deep cavities on the N-peptide coiled-coil trimer that accommodate C-peptide amino acid residues. The amino acid residues which form the cavity have been defined. Thus, a drug (e.g., a peptide, peptidomimetic, small molecule or other agent) which fits into or lines the N-peptide cavity or socket, prevents the N-peptide cavity from accommodating peptides from the C-terminal region of gp41 and, thus, prevents or inhibits gp41 activity, can be identified or designed. For example, a drug which fits into or lines the cavity can be identified or designed, using known methods. One such drug is a molecule or compound which fits into or lines a cavity:

a) lined by Leu-566 of the left N36 helix and Leu-565 of the right N36 helix;
  b) formed on the left side by sidechains from the left N36 helix, including residues (top to bottom) Val-570, Lys-574 (aliphatic portion) and Gln-577;
  c) formed on the right side by residues Leu-568, Trp-571 and Gly-572 of the right N36 helix; and
  d) composed on its floor of Thr-569, Ile-573 and Leu-576.

Figure 6:
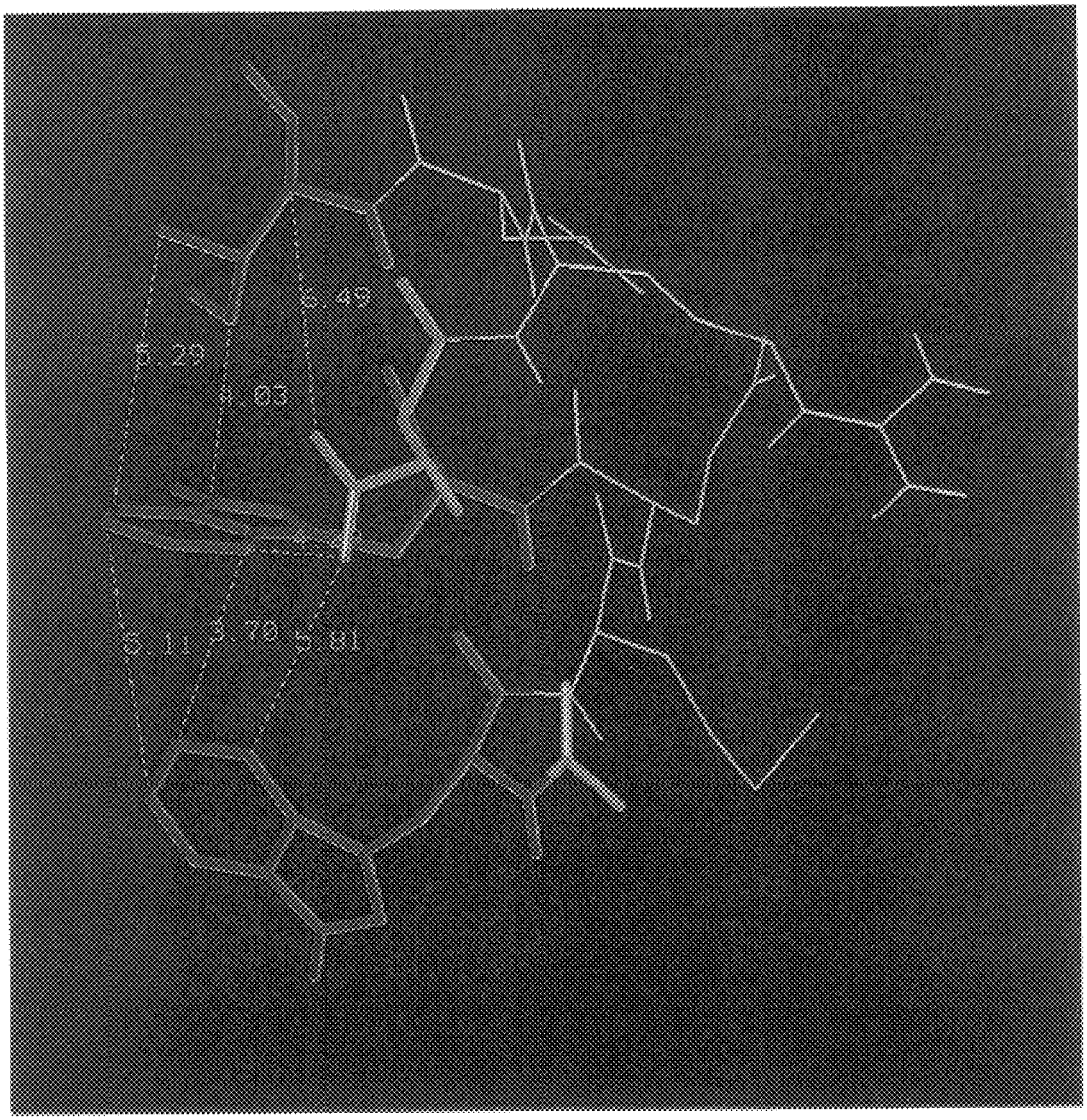
FIG. 6 represents the distances (in Å) between the atoms in the four amino acid residues of C34 that dock into the cavity on the N36 trimer surface. The two tryptophan residues, and the isoleucine residue and the aspartic acid residue are indicated in green.

The cavities present on the N-peptide coiled-coil trimer each accommodate three hydrophobic amino acid residues from the abutting C34 helix: Ile-635, Trp-631 and Trp-628 and a negatively charged amino acid residue from C34: Asp-632, which forms a conserved salt bridge with Lys-574 of N36 immediately to the left of the cavity. A drug which mimics the ability of these three residues (Trp-Trp-Ile) to fit into or line N36 cavities can also be developed. Such a drug can be developed, for example, with reference to the three-dimension coordinates provided (FIGS. 5A–5P) and the information provided (FIG. 6, for example) regarding the distances between the atoms in the four amino acid residues of C34 that dock into the cavity on the N36 trimer surface.

For example, a structure-based approach can be used, along with available computer-based design programs, to identify or design a drug which will fit into, line or bind a cavity or pocket on N36 (or block C34 from doing so) and inhibit or prevent the activity of gp41 and, as a result, reduce (partially or totally) the ability of HIV-1 to infect cells. In one embodiment of the present invention, the following method is carried out to design or identify a molecule or drug which inhibits gp41 activity (and reduces HIV-1 infection of cells) by fitting into or lining the N36 cavity. In a computer processor having a digital processor, a method of designing or identifying a drug or molecule which inhibits (totally or partially) the interaction of N36 and C34 or fits into or lines a cavity on N36, comprises the steps of: (a) providing a library of molecules, compounds or drugs whose crystal structures, coordinates, chemical configurations or structures are known; (b) providing a crystal structure of a target molecule, which is the α-helical domain of the gp41 component of HIV-1 envelope glycoprotein which represents the core of fusion-active gp41 (referred to for convenience as the N36/C34 complex or N36/C34); and (c) comparing coordinates, crystal structure components, chemical configurations or structures of members of the library of molecules with those of the target molecule, such as by using a processor routine executed by the digital processor to search the library to find a molecule or a molecule component which fits into or lines the cavity on N36, the processor routine providing design or identification of a member or members of the library which fit into or line the cavity on N36 or a member or members which comprise a component moiety or component moieties which fit into or line the cavity on N36. For example, this method can be carried out by comparing the members of the library with the crystal structure of gp41 N36/C34 presented herein using computer programs known to those of skill in the art (e.g., Dock, Kuntz, I. D. et al., *Science*, 257:1078–1082 (1992); Kuntz, I. D. et al., *J. Mol. Biol.*, 161:269 (1982); Meng, E. C., et al., *J. Comp.Chem.*, 13:505–524 (1992) or CAVEAT).

In the method, the library of molecules to be searched in (a) can be any library, such as a database (i.e., online, offline, internal, external) which comprises crystal structures, coordinates, chemical configurations or structures of molecules, compounds or drugs (referred to collectively as to be assessed or screened for their ability inhibit N36/C34 interaction candidate N36 ligands). For example, databases for drug design, such as the Cambridge Structural Database (CSD), which includes about 100,000 molecules whose crystal structures have been determined or the Fine Chemical Director (FCD) distributed by Molecular Design Limited (San Leandro, Calif.) can be used. [CSD: Allen, F. H., et al., *Acta Crystallogr. Section B,* 35:2331 (1979)] In addition, a library, such as a database, biased to include an increased number of members which comprise indole rings, hydrophobic moieties and/or negatively-charged molecules can be used.

Coordinates of the molecules in the library can be compared in the method to coordinates of the cavity on N36 or to coordinates of C36 and its components which fit into or line an N36 cavity or pocket. The cavity on N36 is described in detail herein, as are key components of C34 which are accommodated by cavities on the N-peptide. Upon finding a match to coordinates of at least one molecule in the library, at least one member is, thus, determined or identified as an N36 ligand (at least one member is determined to be a member which will inhibit N36/C34 interaction).

Additional steps in the searching process can include combining certain library members or components of library members to form collective coordinates or molecules which combine features or coordinates of two or more library members; comparing the resulting collective coordinates or molecules with the crystal structure of the target molecule and identifying those which will interact with an N36 cavity (or cavities).

Upon identification of an existing drug or design of a novel molecule as described herein, its ability to line or fit into a cavity on N36 or block N36/C34 interaction can be assessed using known methods, such as by expressing N36 and C34 in an appropriate host cell (e.g., a bacterial cell containing and expressing DNA encoding N36 and C34), combining the expressed products with the drug to be assessed and determining whether it interferes with the interaction of N36 and C34, lines a cavity on N36 and C34. Drugs which are found to do so can be assessed in additional assays, both in vitro and in vivo (e.g., an appropriate animal model challenged by HIV infection). Once a drug has been identified or designed, it may be desirable to refine or reconfigure it in such a manner that a drug which binds better (e.g., with greater specificity and/or affinity) is produced. In this case, the processor routine further determines the quality of matches and calculates a goodness of fit, making it possible to do so.

A drug or molecule which binds or fits into a cavity or pocket on the surface of N36, can be used alone or in combination with other drugs (as part of a drug cocktail) to prevent or reduce HIV infection of humans. A drug designed or formed by a method described herein is also the subject of this invention.

Also the subject of this invention is a method of treating an individual infected with HIV or at risk of being infected with HIV, in order to reduce the extent of infection or to prevent infection. In the method, a drug which fits into, lines or binds a cavity or cavities on N36 is administered to the individual, alone or in combination with other drugs.

A further subject of this invention is an immunogen based on a molecule with coordinates as described herein which is used to produce antibodies that bind the N36 cavity or pocket and, thus, prevent N36/C34 interaction and inhibit gp41 activity. For example, the N-peptide core can be used, in known methods, to produce polyclonal or monoclonal antibodies, which can be administered to an individual. Alternatively, an individual (e.g., a human infected with HIV or at risk or being infected) can be immunized with the N-peptide core. The individual will, as a result, produce antibodies which will bind the N36 pocket or cavity and prevent or reduce gp41 activity. Thus, this invention also relates to a vaccine to reduce or prevent gp41 function (and, as a result, HIV infection).

As described above, Applicants have provided the identity of amino acid residues which form the cavity into which amino acid residues of the gp41 C-peptides fit. Thus, they have defined target amino acid residues which can be mutated or modified, individually or jointly, to further assess the structural basis for interaction between the two peptides, identify amino acid residues essential for the two to fit together and design or identify molecules or compounds which inhibit/prevent the two helices from fitting together and, thus, inhibit or prevent gp41 membrane—fusion activity.

Numerous studies have led to the proposal that there are native (nonfusogenic) and fusion-active (fusogenic) states of viral membrane fusion proteins. Extensive conformational changes in the HIV envelope complex are thought to be involved in the transition from the native to the fusogenic state. Binding of CD4 to gp120 exposes the V3 loop of gp120, which likely interacts with the co-receptors. Choe, H. et al., *Cell* 85:1135–1148 (1996); Trkola, A. et al., *Nature* 384:184–187 (1996); Wu, L. et al., *Nature* 384:179–183 (1996). For some laboratory-adapted isolates of HIV-1, the conformational changes in gp120 upon CD4 binding are sufficient to cause gp120 to physically dissociate or "shed" from the viral surface, leaving the membrane-anchored gp41 subunit behind. Hart, T. K. et al., *Proc. Natl. Acad. Sci., USA* 88:2189–2193 (1991); Moore, J. P. et al., *Science* 250:1139–1142(1990). Primary isolates of the virus generally do not shed gp120 readily in the presence of CD4 alone, although CD4 binding still induces conformational changes in gp120. (Sattentau, Q. J. et al., *Phil. Trans. Royal Soc. B* 342:59–66 (1993); Sattentau, Q. J. et al., *J. Virol.* 67:7383–7393 (1993); Sullivan, N. et al., *J. Virol.* 69:4413–4422 (1995), Stamatatos, L. et al., *J. Virol.* 69:6191–6198 (1995)).

CD4 binding also induces conformational changes in gp41, as inferred from changes in antibody binding and sensitivity to limited proteolysis (Sattentau, Q. J. et al., *Phil. Trans. Royal Soc. B* 342:59–66 (1993); Sattentau, Q. J. et al., *J. Virol.* 67:7383–7393 (1993)). Moreover, addition of low levels of soluble CD4 enhances the infectivity of some viral isolates, suggesting that the gp120/gp41 conformational changes induced by CD4 play a role in membrane fusion (Allan, J. S. et al, *Science* 247:1084–1088 (1990); Sullivan, N. et al., *J. Virol.* 69:4413–4422 (1995)). These conformational changes are thought to expose the hydrophobic, glycine-rich fusion-peptide region of gp41 that is essential for membrane-fusion activity.

To obtain a detailed structure for gp41, a protein-dissection approach, in which key substructures of a protein are identified and studied was applied. See, for example, Oas, T. G. et al., *Nature* 336:42–48 (1988). Limited proteolysis of a fragment corresponding to the ectodomain of gp41 generated a stable, soluble complex composed of two peptide fragments denoted N51 and C43 (FIG. 1) that are derived from the N- and C-terminal regions of the ectodomain, respectively (Lu, M. et al., *Nature Struct. Biol.* 2:1075–1082 (1995)). In gp41, the region following the fusion peptide has a high α-helical propensity and a 4-3 heptad repeat of hydrophobic residues, a sequence feature characteristic of coiled coils. Chambers, P. et al., *J. Gen. Virol.* 71:3075–3080 (1990); Delwart, E. L. et al., *AIDS Res.*

*Hum. Retroviruses* 6:703–706 (1990); Gallaher, W. R. et al., *AIDS Res. Hum. Retroviruses* 5:431–440 (1989). The N51 peptide corresponds to the 4-3 hydrophobic repeat region adjacent to the fusion peptide, while the C43 peptide is derived from the region prior to the transmembrane segment (FIG. 1).

Interestingly, isolated peptides that overlap, or are derived from, the N51 and C43 regions of gp41 can have potent anti-viral activity (Wild, C. T. et al., *Proc. Natl. Acad. Sci., USA* 89:10537–10541 (1992); Wild, C. T. et al, *Proc. Natl. Acad. Sci., USA* 91:9770–9774 (1994); Jiang, S. et al., *Nature* 365:113 (1993)). Peptides from the C-terminal region of the ectodomain have the highest activity. Consistent with these studies, both N51 and C43 are capable of inhibiting HIV envelope-mediated cell fusion; the C43 peptide exhibits 10-fold greater activity than N5 1 (Lu, M. et al., *Nature Struct. Biol.* 2:1075–1082 (1995)). The inhibitory activity of the C43 peptide, however, is markedly reduced when stoichiometric amounts of N51 are present, suggesting that the C43 peptide inhibits membrane fusion in a dominant-negative manner, by associating with an N51 region within intact gp41 (Lu, M. et al., *Nature Struct. Biol.* 2:1075–1082 (1995)). Thus, in addition to providing insights into the mechanism of membrane fusion, determining the structural basis for interaction between the N51 and C43 regions will assist anti-viral drug-development efforts.

Biophysical studies showed that the N51 and C43 peptides associate to form a highly thermostable, helical, trimeric complex of heterodimers, in which the N51 and C43 helices are oriented in an antiparallel manner. Lu, M. et al., *Nature Struct. Biol.* 2:1075–1082 (1995). Analogous experiments with the gp41 ectodomain from simian immunodeficiency virus (SIV) gave almost identical results, indicating that the gp41 core identified in these protein-dissection studies is conserved among lentiviruses. Blacklow, S. C. et al., *Biochemistry* 34:14955–14962 (1995). On the basis of these results and other considerations, we proposed that the gp41 core consists of an interior coiled-coil trimer formed by the N51 region, against which three C43 helices pack. Lu, M. et al., *Nature Struct. Biol.* 2:1075–1082 (1995); Blacklow, S. C. et al., *Biochemistry* 34:14955–14962 (1995).

The thermal denaturation of the N51/C43 complexes from HIV-1 or SIV gp41 is irreversible, probably as a result of aggregation of the unfolded peptides at high temperature. Lu, M. et al., *Nature Struct. Biol.* 2:1075–1082 (1995); Blacklow, S. C. et al., *Biochemistry* 34:14955–14962 (1995). With a view towards crystallographic studies, further protein dissection experiments were used to define a smaller subdomain with more favorable thermodynamic properties. These studies led to the identification of the peptides N36 and C34 (FIG. 1). Like the longer peptides, N36 and C34 form a stable, trimeric complex of heterodimers with 100% α-helix content. Unlike the larger complex, however, the N36/C34 complex has a reversible thermal unfolding transition. Presented herein is the crystal structure of the N36/C34 complex solved to 2.0 Å resolution, as well as a discussion of the implications of this structure for HIV viral membrane fusion and its inhibition.

The work described herein provides good evidence that the structure of gp41 obtained is found in the fusion-active state of HIV envelope. That this is the core of gp41 in the fusogenic state is supported by several considerations.

First, the N36/C34 complex folds in the absence of gp120. The fusogenic state of gp41 is expected to be stable in the absence of gp120, since dissociation of gp120 from the envelope glycoprotein is thought to accompany the conversion from a native to a fusogenic state. Cohen, J., *Science* 274:502 (1996); Wilkinson, D., *Current Biology* 6:1051–1053, (1996). Similarly, the conversion of influenza HA2 to the fusogenic state is accompanied by loss of most of its contacts with HA1. Proteolysis of the low-pH converted form of HA prior to crystallization removes most of the receptor-binding HA1 subunit. Bullough, P. A. et al., *Nature* 371:37–43 (1994). Moreover, the structural features of the fusogenic state are preserved in fragments of HA2 that fold cooperatively in the complete absence of the HA1 subunit. Carr, C. M. et al., *Cell* 73:823–832 (1993); Chen, J. et al., *Proc. Natl. Acad. Sci., USA* 92:12205–12209 (1995).

Second, the isolated gp41 core is exceedingly stable to thermal denaturation. The N51/C43 complex has an apparent melting temperature of approximately 90° C. Lu, M. et al., *Nature Struct. Biol.* 2:1075–1082 (1995). In contrast, the native state of the HIV envelope glycoprotein is not particularly stable, as evidenced by the ease with which gp120 is shed in preparations of virus particles. Helseth, E. et al., *J. Virol.* 65:2119–2123 (1991); Kalyanaraman, V. S. et al., *AIDS Res. Hum. Retroviruses* 6, 371–380 (1990).

Third, mutations in gp41 that abolish infectivity and membrane fusion often map to residues that are expected to stabilize the gp41 core structure determined here. Numerous studies show that mutations in the 4-3 hydrophobic repeat region abolish membrane fusion, although these mutants tend to have additional defects. Dubay, J. W. et al., *J. Virol.* 66:4748–4756 (1992); Chen, S. S., *J. Virol.* 68:2002–2010 (1994); Chen, S. S. et al., J. Virol. 67, 3615–3619 (1993); Wild, C. et al., *Proc. Natl. Acad. Sci., USA* 91:12676–12680 (1994); Poumbourios, P.,*J. Virol.* 71:2041–2049 (1997). The Leu-568→Ala, Trp-571→Arg, and Asn-656→Leu mutations are particularly noteworthy because cells expressing mutant envelope glycoproteins with one of these point mutations are completely defective in membrane fusion, as judged by an inability to form syncytia with CD4-positive human lymphocyte lines, even though the mutant proteins exhibit substantial cell-surface expression, CD4 binding, gp120/gp41 association, gp160 precursor processing, and soluble CD4-induced shedding. Cao, J. et al., *J. Virol.* 67:2747–2755 (1993). Leu-568 and Trp-571 are N36 residues that line the right wall of the cavity. Asn-656 is in an a position of the C34 peptide and packs against the central N36 coiled-coil trimer. The locations of these key mutations suggest that interactions between the N36 and C34 helices are critical for membrane fusion.

Fourth, that the N36/C34 structure corresponds to the core of the fusogenic state of gp41 is consistent with a large body of data on the inhibition of HIV-1 infection and syncytia formation by derivatives of the peptides that make up this core. This issue is discussed in more detail below. Finally, the structural similarity of the N36/C34 complex to the low-pH induced conformation of influenza HA2 (Bullough, P. A. et al., *Nature* 371:37–43 (1994)) and to the structure of Mo-MLV TM (Fass, D. et al., *Nature Struct. Biol.* 3:465–469 (1996)), each of which has been proposed to represent fusion-active conformations, supports the idea that N36/C34 is the core of the fusogenic conformation of gp41. For all three structures, the hydrophobic fusion peptide would be immediately amino terminal to a central, three-stranded coiled coil. In influenza HA2 and HIV-1 gp41, the central three-stranded coiled coils are each stabilized by three helices that pack obliquely against the coiled-coil trimer in an antiparallel manner. In the TM subunit of Mo-MLV, these obliquely packed helices are replaced by a short helix and an extended region that serve a similar structural role.

Work described herein also relates to inhibitors of HIV-1 infection and targets for developing new peptidomimetic or small-molecule inhibitors of HIV infection. Synthetic peptides containing approximately 40 residues from gp41 that overlap, or include all of, the residues in N36 or C34 can be effective inhibitors, at micromolar to nanomolar concentrations, of HIV infection and syncytia formation. Lu, M. et al., *Nature Struct. Biol.* 2:1075–1082 (1995); Jiang, S. et al., *Nature* 365:113 (1993); Wild, C. T. et al., *Proc. Natl. Acad. Sci., USA* 89:10537–10541 (1992); Wild, C. T. et al., *Proc. Natl. Acad. Sci. USA,* 91:9770–9774 (1994). Assessment previously of the inhibitory properties of the N51 and C43 peptides implied that these peptides work in a dominant negative manner (Herskowitz, I., *Nature* 329:219–222 (1987)) by binding to viral gp41 (Lu, M. et al., *Nature Struct. Biol.* 2:1075–1082 (1995)), a conclusion that was also reached through studies of a gp41 ectodomain chimeric protein (Chen, C. H. et al., *J. Virol.* 69:3771–3777 (1995)). Further evidence in support of a dominant-negative mechanism is provided by the finding that mutations in C-peptide derivatives that disrupt their interactions with N-peptide correlate with decreased potency as inhibitors. Wild, C. et al., *AIDS Res. Hum. Retroviruses* 11:323–325 (1995).

Figures 3A, 3B:
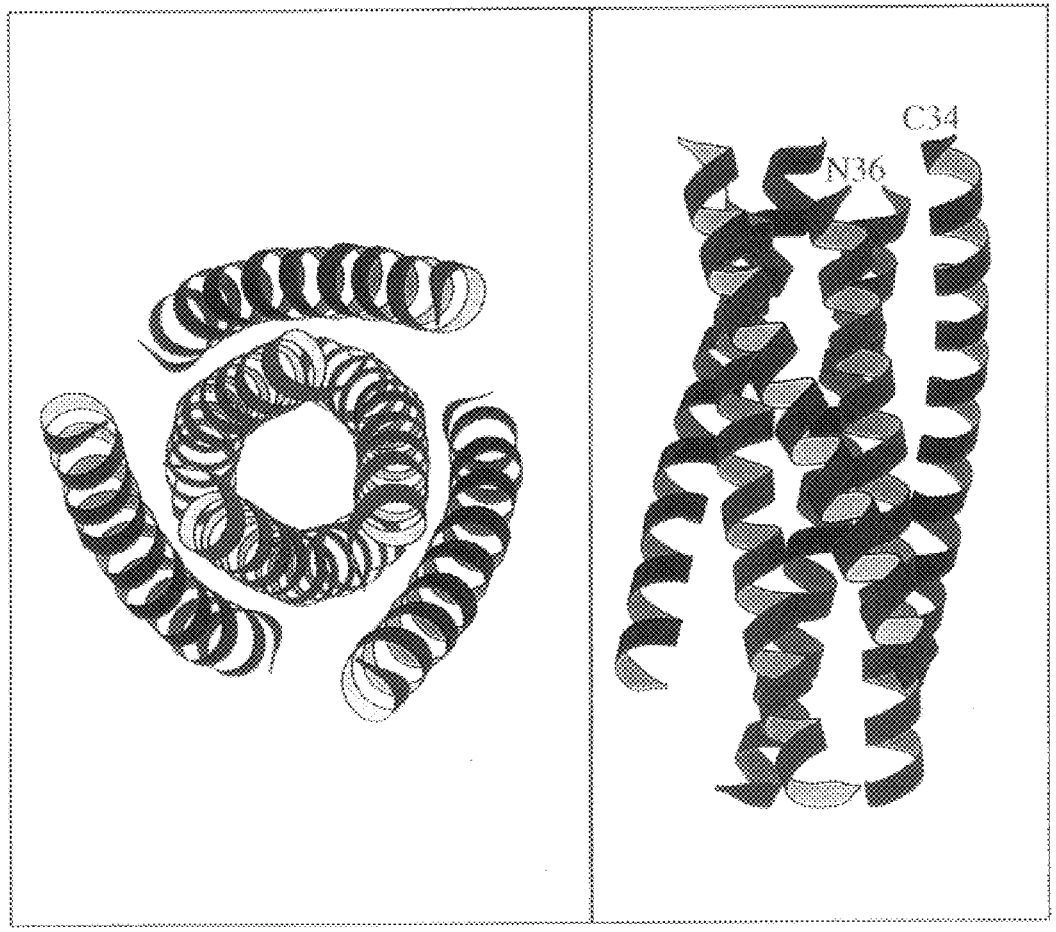
FIGS. 3A and 3B present overall views of the N36/C34 complex.
Figure 4:
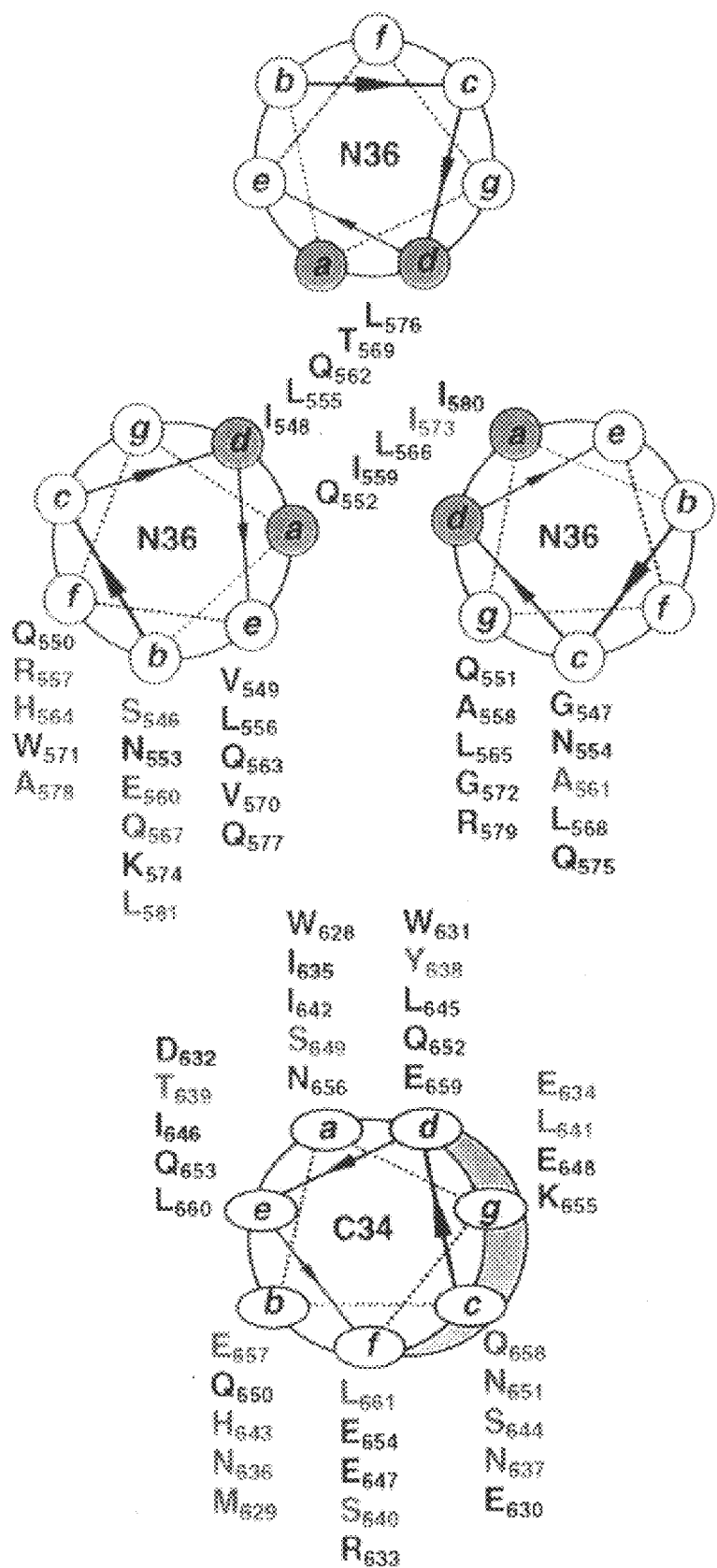
FIG. 4 shows a helical wheel representation of N36 and C34; three N36 helices and one C34 helix are represented as helical wheel projections. The view is from the top of the complex, as in FIG. 3A. The residues at each position are represented by the single-letter codes for amino acids. The N36 helices interact through "knobs-into-holes" packing interactions at the a and d positions. Positions of the N36 and C34 helices that occupy the interhelical space between two N36 helices and a C34 helix are shown (arrows). The helical wheel positions in C34 are indicated by ellipses to represent the oblique orientation of this helix relative to N36. At the top of the complex, C34 is slightly tilted towards the left N36 helix, while at the bottom of the complex, it is slightly tilted towards the right N36 helix.

The gp41 core crystal structure is fully consistent with this dominant-negative mechanism of inhibition (FIG. 3). The C-peptide derivatives could act as dominant-negative inhibitors by binding to the endogenous N-peptide coiled-coil trimer within viral gp41. The N-peptides might inhibit fusion by interfering with formation of the central, coiled-coil trimer within viral gp41, and/or by binding to endogenous viral C-peptide regions.

Both the N- and C-peptide classes of inhibitors are effective against a wide range of HIV strains, including laboratory-adapted strains and primary isolates. Wild, C. T. et al., *Proc. Natl. Acad. Sci., USA* 89:10537–10541 (1992); Jiang, S. et al., *Nature* 365:113 (1993); Wild, C. T. et al., *Proc. Natl. Acad. Sci., USA* 91:9770–9774 (1994). In contrast, soluble CD4 and many neutralizing antibodies are typically effective only on a limited subset of HIV strains (e.g., Daar, E. S. et al., *Proc. Natl. Acad. Sci., USA* 87:6574–6578 (1990); Palker, T. J. et al., *Proc. Natl. Acad. Sci., USA* 85:1932–1936 (1988); Nara, P. L. et al., *J. Virol.* 62:2622–2628 (1988); Moore, J. P. et al., *J. Virology* 69:101-109 (1995). There is a striking conservation of residues involved in interactions between the N-peptide and C-peptide, comparing gp41 from HIV-1 and SIV. The broad neutralizing effects of the N- and C-peptides derive from the strong sequence conservation of these residues.

The highly conserved, deep cavities on the N-peptide coiled-coil trimer that accommodate conserved C-peptide residues are useful targets for the development of new peptidomimetic or small-molecule inhibitors of HIV infection. The two indole rings and neighboring sidechains that occupy the prominent cavity in N36 are a particularly attractive target for the design and/or development of new drugs or identification of existing drugs which inhibit HIV infection. Not only is this cavity deep and highly conserved, but two of the three key mutations that disrupt membrane fusion, discussed above, map to one wall of this cavity. Because some of the known potent peptide inhibitors (Wild, C. T. et al., *Proc. Natl. Acad. Sci., USA* 91:9770–9774 (1994)) extend beyond N36 and C34 and do not involve this cavity region, it is likely that other distinctive surface features exist in the interface between the N- and C-helices of longer peptides such as N51 and C43. Lu, M. et al., *Nature Struct. Biol.* 2:1075–1082 (1995). The importance of identifying drugs that target the HIV membrane-fusion machinery is emphasized by the success of combination drug regimens for the treatment of AIDS. As yet, these combination therapies do not target the HIV envelope. A method of identifying a drug which is an inhibitor of N36/C34 peptide interaction (and, thus, is an inhibitor of the HIV membrane fusion machinery and, as a result, reduces or prevents HIV entry into (infection of) cells is the subject of this invention. In the method, N36 and C34 are combined with a drug to be assessed, under conditions suitable for N36 and C34 to interact (suitable for cavities on the N-peptide coiled-coil trimer to accommodate C-peptide amino acid residues). The resulting combination is maintained under these conditions for sufficient time to permit N36 and C34 to interact (e.g., for sufficient time for N36 and C34 to interact in the absence of the drug being assessed). Whether interaction occurs and/or the extent to which N36 and, C34 interact is assessed, using known methods. If N36 and C34 do not interact or interact to a lesser extent in the presence of the drug being assessed than in the absence of the drug, the drug to be assessed is an inhibitor of N36/34 interaction. Such a drug is an inhibitor of the HIV membrane fusion machinery. Such an inhibitor can be further assessed, using in vitro or in vivo methods, for its ability to reduce or prevent HIV entry into cells.

Results of the work described have implications for gp41 function and viral membrane fusion. The structures of the cores of the membrane-fusion subunits from HIV, Mo-MLV and influenza virus are remarkably similar. It appears that these diverse viruses present fusion peptides to target cells via a common scaffold, in which the fusion peptides are atop a central, three-stranded coiled coil that is supported by additional, carboxy-terminal structures. This scaffold is likely to be a common feature of viral membrane-fusion proteins since many of these proteins contain coiled-coil signature sequences, with 4-3 heptad repeats of hydrophobic amino acids, adjacent to an amino-terminal fusion-peptide region. Delwart, E. L. et al., *AIDS Res. Hum. Retroviruses* 6:703–706 (1990); Chambers, P. et al., *J. Gen. Virol.* 71:3075–3080 (1990); Gallaher, W. R. et al., *AIDS Res. Hum. Retroviruses* 5:431–440 (1989). Moreover, studies of the fusion proteins of several paramyoviruses have identified regions with similarity to the N- and C-peptide regions of HIV and SIV gp41 (Lambert, D. M. et al., *Proc. Natl. Acad. Sci., USA* 93:2186–2191 (1996)). These common structural features suggest that the rich body of work investigating the mechanism of membrane fusion for many other viruses, including influenza, is relevant for understanding the mechanism of HIV-mediated membrane fusion.

Given the similarity in structure between the HIV gp41 core and the low-pH converted conformation of HA2, it is worth considering whether the structural rearrangements that occur during the transition of HA2 to the fusogenic state are analogous to those in gp41. In the native, non-fusogenic conformation of influenza HA, part of the N-terminal coiled-coil trimer seen in the fusogenic state (Bullough, P. A. et al., *Nature* 371:37–43 (1994)) is held in a non-helical, hairpin structure, as a result of extensive interactions with the receptor-binding HA1 subunit (Wilson, I. A. et al., *Nature* 289:366–373 (1981)). Thus, the receptor-binding HA1 subunit acts as a "clamp" that binds this N-terminal region of HA2, holding it in the non-coiled coil conformation. The receptor-binding domains dissociate in the fusogenic conformation of HA, as in HIV, although in the case of influenza, the HA1 subunits are still tethered via a disulfide bond to HA2. Upon release of the HA1 clamp, a dramatic conformational change in HA2 occurs, including coiled-coil formation by this N-terminal region (Bullough, P. A. et al., *Nature* 371:37–43 (1994); Carr, C. M. et al., *Cell* 73:823–832 (1993)).

A substantial conformational change in the envelope glycoprotein complex also appears to be critical during HIV infection, although few details are understood. It remains to be determined whether the HIV envelope complex also utilizes coiled-coil formation as part of a spring-loaded mechanism, or if the gp41 core structure determined here is present in the native as well as the fusogenic state. It is possible that the N36/C34 structure is the core structure of gp41 even when it is bound to gp120, and that release of gp120 simply exposes the fusion-peptide region of gp41. Alternatively, HIV gp120, like influenza HA1, may serve as a clamp that represses formation of the N36/C34 structure presented here, with gp120 shedding allowing its formation. This gp41 core structure serves as the starting point for addressing this and other essential structural questions about the mechanism of HIV entry into cells.

The present invention is illustrated by the following examples, which are not intended to be limiting in any way.

EXAMPLES

The materials and methods described below were used in the examples which follow.

Materials and Methods

Peptide Purification and Crystallization

Peptides N36 and C34 were synthesized by standard FMOC peptide chemistry and have an acetylated N-terminus and a C-terminal amide. N36 corresponds to residues 546 to 581 of gp160, while C34 corresponds to residues 628 to 661. After cleavage from the resin, the peptides were desalted on a Sephadex G-25 column (Pharmacia) and lyophilized. Peptides were then purified by reverse-phase high performance liquid chromatography (Waters, Inc.) on a Vydac C18 preparative column. The identity of the peptides was verified by mass spectrometry. Peptide concentration was determined by tyrosine and tryptophan absorbance in 6 M GuHCl. Edelhoch, H., *Biochemistry* 6:1948–1954 (1967).

To grow crystals, a 10 mg/ml stock of the N36/C34 complex was diluted 1:1 in a sitting drop with 80 mM $NH_4Cl$, 20% PEG200, and 50% isopropanol and allowed to equilibrate against a reservoir of 80 mM $NH_4Cl$, 20% PEG200, and 30% isopropanol. Crystals grew as hexagonal prisms and belonged to the space group P321 (a=b=49.5 Å, c=55.3 Å). For native data sets and heavy atom screens, crystals were flash-frozen in a MSC cryogenic crystal cooler (X-stream), and data was collected on a Rigaku RU-200 rotating-anode X-ray generator with an R-axis IIc detector.

Heavy Atom Screen and Phase Determination

Multiwavelength anomalous diffraction (MAD) data were collected at the Howard Hughes Medical Institute beamline X4A of the National Synchrotron Light Source at Brookhaven National Laboratory. Fluorescence spectra (1.1459 to 1.1354 Å) were obtained from a single flash-frozen crystal soaked in 0.04% $OsO_4$ in harvest buffer (80 mM $NH_4Cl$, 20% PEG200, 30% isopropanol) for 4 hours. Based on the fluorescence profile, individual data sets were collected on Fuji imaging plates at four wavelengths ($l_1$=1.1396 Å, $l_2$=1.1398 Å, $l_3$=1.1402 Å, and $l_4$=1.1344 Å). Reflections were integrated and scaled with DENZO and SCALEPACK. (Otwinowski, Z., *Daresbury Study Weekend Proceedings*, 1993.)

Data merging, phase determination and map generation were all performed using the CCP4 suite of programs. CCP4, *Acta Cryst.* D50:760–763 (1994). Anomalous and dispersive difference Patterson maps from MAD data sets all showed a single clear peak corresponding to the osmium binding site. The position of the site was calculated from the single z=0 Harker section and from cross peaks found at z=0.28 and z=0.71. Phases generated with the program MLPHARE (Otwinowski, Z., *Daresbury Study Weekend Proceedings*, 1991) gave an overall figure of merit of 0.89 (Table) and produced an interpretable electron density map with a clear solvent boundary. Density modification was subsequently performed using DM (Cowtan, K. D., *Newsletter on Protein Crystallography* 31:34–38 (1994)), resulting in maps of high quality in which electron density for the entire main chain and all side chains was evident.

Model Refinement

The polypeptide chain was traced and the side chains readily positioned into a 2.7 Å density-modified map using the program O (Jones, T. A., and Kjeldgaard, M., *O— The Manual*, Uppsala, Sweden: http://kaktus.kemi.aau.dk, 1992). The initial model of N36/C34 was refined with the program XPLOR (Brünger, A. T., *A system for X-ray crystallography and NMR. X-PLOR Version* 3.1, Yale University Press, New Haven, Connecticut, 1992) against data to 2.0 Å from a native crystal. An anisotropic B-factor was applied to the native structure factors using XPLOR, and a free R set (Brünger, A. T., *Nature* 355:472–475 (1992)) was taken from the data prior to refinement (Table). The model was refined by iterative cycles of grouped B-factor, positional, and individual B-factor refinement. As the refinement proceeded, 43 waters were added and a bulk solvent correction was applied. At no time during the refinement did the molecule differ enough from the original model so as to require manual rebuilding, though main chain and side chain geometries were optimized in O between cycles of refinement. The quality of the structure was verified by PROCHECK (Laskowski, R. A. et al., *J. Appl. Cryst.* 26:283–291 (1993)), with all residues but one (Ile-580) occupying most-preferred regions of Ramachandran space. Ile-580 lies in the additionally allowed region of Ramachandran space and is the second residue from the C-terminus of the N36 peptide; inspection of the solvent-flattened MAD-phased maps confirmed its position.

Example 1

Production of Crystals of N36/C34

Figure 2:
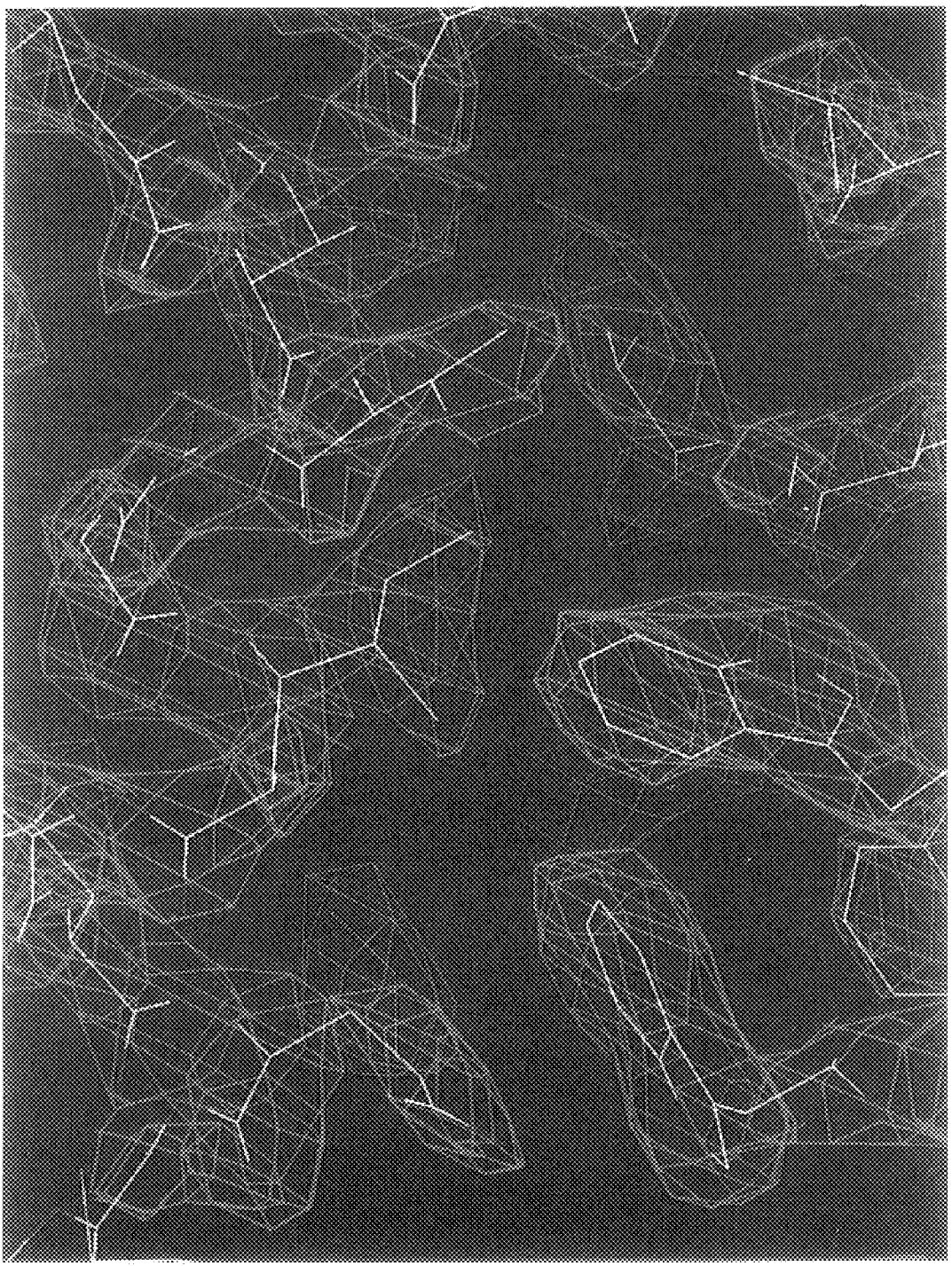
FIG. 2 is a representative portion of the initial electron density map calculated using experimental structure-factor amplitudes and solvent-flattened MAD phases, shown with the refined molecular model. The map is contoured at 1.5 standard deviations above the mean density. The figure was generated with the program O (Jones, T. A., and Kjeldgaard, M., *O—The Manual,* Uppsala, Sweden: http://kaktus.kemi.aau.dk (1992)).

Crystals of N36/C34 were grown by sitting-drop vapor diffusion (see Methods). An initial model of the complex was built into an electron density map generated by multiwavelength anomalous dispersion (MAD) analysis (Hendrickson, W. A., *Science* 254:51–58 (1991)) of an osmium-derivatized crystal. Details of data collection and MAD phasing statistics are listed in the Table. A representative portion of the solvent-flattened electron density map used for building the initial model is shown in FIG. 2. The structure was refined against data to 2.0 Å from a native crystal to yield an $R_{free}$ of 0.266 and an $R_{cryst}$ of 0.238 (Table).

TABLE

Crystallographic and refinement statistics

Data collection

| Crystal | λ (Å) | % complete | $R_{sym}$[1] (%) | Resol. (Å) |
|---|---|---|---|---|
| Native | 1.5418 | 96.5 | 5.5 | 2.0 |
| $OsO_4$ λ1 | 1.1398 | 96.4 | 4.3 | 2.7 |
| $OsO_4$ λ2 | 1.1396 | 96.4 | 4.3 | 2.7 |
| $OsO_4$ λ3 | 1.1344 | 96.8 | 4.5 | 2.7 |
| $OsO_4$ λ4 | 1.1406 | 93.4 | 4.5 | 2.7 |

Phasing statistics (12–2.7 Å)

| Derivative | $R_{iso}$[2] (%) | $R_{diff}$[3] (%) (weight) | $R_{cullis}$[4] Acentric | $R_{cullis}$[4] Centric | $R_{cullis}$[4] Anom. | Ph. power[5] Acentric | Ph. power[5] Centric | Occ.[6] | Anom. Occ.[6] |
|---|---|---|---|---|---|---|---|---|---|
| $OsO_4$ λ1 vs. λ4 | 4.4 | 6.7 | 0.46 | 0.53 | 0.21 | 2.46 | 1.53 | 0.075 | 2.165 |
| $OsO_4$ λ2 vs. λ4 | 6.6 | 9.3 | 0.37 | 0.37 | 0.22 | 3.34 | 2.36 | 0.132 | 1.784 |
| $OsO_4$ λ3 vs. λ4 | 5.4 | 7.4 | 0.42 | 0.44 | 0.35 | 2.94 | 2.12 | 0.105 | 1.005 |

Overall figure of merit (before solvent flattening): 0.89

Refinement statistics (12–2.0 Å)

| Non-hydrogen protein atoms | Waters | Number of reflections working | Number of reflections free | $R_{cryst}$[7] | $R_{free}$[7] | R.m.s. deviations bonds (Å) | R.m.s. deviations angles (°) |
|---|---|---|---|---|---|---|---|
| 596 | 43 | 5212 | 371 (7.12%) | 0.238 | 0.266 | 0.014 | 2.742 |

[1] $R_{sym} = \Sigma\Sigma_j |I_j - \langle I \rangle| / \Sigma I \langle I \rangle$, where $I_j$ is the recorded intensity of the reflection j and $\langle I \rangle$ is the mean recorded intensity over multiple recordings.
[2] $R_{iso} = \Sigma ||F_{\lambda i} \pm F_{\lambda 4}| - |F_{\lambda i}|| / \Sigma |F_{\lambda 4}|$, where $F_{\lambda i}$ is the structure factor at wavelength λi and $F_{\lambda 4}$ is the structure factor at the reference wavelength λ4.
[3] $R_{diff} = [\Sigma |(F^2_{(\lambda 4)} - \Phi_{mean}) / \phi F^2_{(\lambda 4)}| + |(F^2_{(\lambda i)} - \Phi_{mean}) / \phi F^2_{(\lambda i)}|] / [\phi|(F^2_{(\lambda 4)}/\phi F^2_{(\lambda 4)}) + (F^2_{(\lambda i)} / \phi F^2_{(\lambda i)})|]$, where $\Phi_{mean} = [(F^2_{(\lambda 4)} / \phi F^2_{(\lambda 4)}) + (F^2_{(\lambda i)} / \phi F^2_{(\lambda i)})] / [(1 / \phi F^2_{(\lambda 4)}) + (1 / \phi F^2_{(\lambda i)})]$ and $\phi F^2_{(n)} = [\text{Variance}(F^2_{(n)})]4F^2_{(n)}$.
[4] $R_{cullis} = \Sigma ||F_{\lambda i} \pm F_{\lambda 4}| - |F_{h(\lambda i),c}|| / \Sigma |F_{\lambda I} \pm F_{\lambda 4}|$, where $F_{h(\lambda i),c}$ is the calculated heavy atom structure factor.
[5] Phase power = $\langle F_{h(\lambda i)} \rangle / E$, where $\langle F_{h(\lambda i)} \rangle$ is the root-mean-square heavy atom structure factor and E is the residual lack of closure error.
[6] Occupancies are values output from MLPHARE.
[7] $R_{cryst, free} = \Sigma ||F_{obs}| - |F_{calc}|| / |F_{obs}|$, where the crystallographic and free R factors are calculated using the working and free reflection sets, respectively.

Example 2
Assessmetn of the Structure of the N36/C34 Complex

The N36/C34 complex is a six-stranded helical bundle (FIG. 3). The center of this bundle consists of a parallel, trimeric coiled coil of three N36 helices wrapped in a gradual left-handed superhelix. Three C34 helices wrap antiparallel to the N36 helices in a left-handed direction around the outside of the central coiled-coil trimer. The complex is a cylinder measuring ~35 Å in diameter and ~55 Å in height.

As in other naturally-occurring coiled coils (Cohen, C. et al., *Proteins* 7:1–15 (1990)), the interior residues at the a and d positions of the N36 heptad repeat are predominantly hydrophobic, although occasional buried polar interactions are also present in the central three-stranded coiled coil (FIG. 4). A sequence comparison of HIV-1 (HXB2 strain) and SIV (Mac239 strain) gp41 shows that the residues at these two heptad-repeat positions are highly conserved (FIG. 4). The characteristic "knobs-into-holes" packing of coiled coils is utilized, whereby the residues (knobs) at the a and d layers pack into cavities (holes) between four residues of an adjacent helix (Crick, F. H. C., *Acta Cryst.* 6:689–697 (1953); O'Shea, E. K. et al, *Science* 254:539–544 (1991)). Of the three types of knobs-into-holes packing geometry observed in coiled-coil structures (Harbury, P. B. et al., *Science* 262:1401–1407 (1993); Harbury, P. et al, *Nature* 371:80–83 (1994)), the N36 trimer demonstrates exclusively "acute" packing geometry, similar to that found in the crystal structure of an isoleucine-zipper trimer (Harbury, P. et al., *Nature* 371:80–83 (1994)). This type of packing arrangement in the interior of the coiled coil is characteristic of trimers because it allows β branched residues (e.g., isoleucine) to pack favorably at both the a and d positions (Harbury, P. et al., *Nature* 371:80–83 (1994)). Trimeric coiled coils, like the N36 trimer (FIG. 4), tend to have β branched residues at both the a and d positions.

Although complexes of the N- and C-peptides are clearly trimeric (Lu, M. et al., *Nature Struct. Biol.* 2:1075–1082 (1995); Blacklow, S. C. et al., *Biochemistry* 34:14955–14962 (1995)), isolated N-peptides corresponding to the 4-3 hydrophobic repeat from gp41 have been reported to form tetramers, leading to conflicting conclusions regarding the oligomeric state of gp41 (Lawless, M. et al, *Biochemistry* 30 35:13697–13708 (1996); Rabenstein, M. et al., *Biochemistry* 34:13390–13397 (1995); Rabenstein, M. D. et al., *Biochemistry* 35:13922–13928 (1996); Shugars, D. C. et al., *J. Virol.* 70:2982–2991 (1996)). An electrostatic potential map of the N36 coiled-coil trimer shows that its surface is largely uncharged. The grooves that are the sites for C34 interaction are lined with predominantly hydrophobic residues (see below) that would be expected to lead to aggregation upon exposure to solvent. Indeed, previous studies have shown that the isolated N-peptides tend to aggregate (Blacklow, S. C. et al., *Biochemistry* 34:14955–14962 (1995); Lu, M. et al., *Nature Struct. Biol.* 2:1075–1082 (1995)). Thus, conclusions regarding the oligomerization state of gp41 based on studies of isolated N-peptides are probably misleading. The N36/C34 complex shows a much more highly charged surface due to acidic residues on the outside of the C34 helices, explaining the greater solubility of the heterodimeric complex.

Example 3
Determination of Interactions Between the N- and C-Peptide Helices

Three C34 helices pack obliquely against the outside of the N36 coiled-coil trimer in an antiparallel orientation. These C34 helices interact with N36 mainly through hydrophobic residues in three grooves on the surface of the central coiled-coil trimer. Sequence comparisons between HIV and SIV gp41 shows that the residues lining these grooves are highly conserved. In contrast, the N36 residues flanking the C34 helices are divergent between HIV and SIV.

This pattern of sequence conservation is also apparent on a helical wheel representation of three N36 helices and one C34 helix (FIG. 4). In this diagram, the residue positions in C34 are depicted as ellipses to indicate the oblique tilt of the C34 helix relative to the N36 superhelix and to emphasize that C34 is not part of a coiled coil. Residues at the e and g positions of the N36 helices lie on the outside of the central coiled coil and point into the triangular interhelical space between two N36 helices and a buttressing C34 helix. In general, residues at positions a and d of C34 pack against residues at the e and g positions of the N36 helices (FIG. 4), although contacts at other positions are often observed. Comparing HIV and SIV gp41, no nonconservative changes exist at the e and g positions of the N36 helix, and only two such changes occur at the a and d positions of C34. In contrast, 8 of the 9 nonconservative changes in the N36 helix occur at the outside f, b, and c positions, while 13 of the 15 nonconservative changes in the C34 helix occur at positions other than a and d. The sequence of the N-peptide region of gp41 is among the most highly conserved within the HIV envelope glycoprotein. Our results show that the high sequence conservation in this region results from selective pressure on the e and g positions to retain C34 peptide interactions, as well as pressure on the a and d positions to maintain trimeric coiled-coil interactions.

Each of the grooves on the surface of the N36 trimer has a particularly deep cavity. This cavity is large (~16 Å long, ~7 Å wide, and 5–6 Å deep) and accommodates three hydrophobic residues from the abutting C34 helix: Ile-635, Trp-631 and Trp-628. The top of the cavity is lined by Leu-566 of the left N36 helix and Leu-565 of the right N36 helix. Side chains from the left N36 helix form the left side of the cavity, including residues (top to bottom) Val-570, Lys-574 (aliphatic portion), and Gln-577. The right wall is formed by residues Leu-568, Trp-571, and Gly-572 of the right N36 helix. The floor of the cavity is composed of Thr-569 and Leu-576 of the right N36 helix, and also Ile-573 of both N36 helices. With the exception of Ile-573 (which is replaced by Thr), all the residues forming the cavity are identical between HIV-1 and SIV. In addition to these predominately hydrophobic interactions within the cavity, Asp-632 of C34 forms a conserved salt bridge with Lys-574 of N36 immediately to the left of the cavity.

Example 4
Comparison of the Structure of the N36/C34 Complex with the Low-pH Incuced Conformation of HA The N36/C34 complex shows striking structural similarity to the low-pH induced conformation of the influenza $HA_2$ subunit ($TBHA_2$) (Bullough, P. A. et al., *Nature* 371:37–43 (1994)) and to the TM subunit of Mo-MLV (Fass, D. et al., *Nature Struct. Biol.* 3:465–469 (1996)), each of which has been proposed to be a fusogenic conformation. Remarkably, the core of each of the three structures contains a three-stranded coiled coil that would be adjacent to the amino-terminal fusion peptide. The trirneric coiled coil of gp41 is very similar to that of the Mo-MLV TM, both having a similar superhelical pitch (~175 Å) and a regular 4-3 periodicity. In contrast, the $TBHA_2$ coiled coil is atypical because it contains two regions with skips in the 4-3 periodicity, resulting in an underwound superhelix (pitch of 300–400 Å). As in the gp41 core structure, $TBHA_2$ contains three antiparallel helices that are packed, with a left-handed tilt, against the central trimeric coiled coil.

Equivalents

While this invention has been particularly shown and described with references to preferred embodiments thereof, it will be understood by those skilled in the art that various changes in form and details may be made therein without departing from the spirit and scope of the invention as defined by the appended claims. Those skilled in the art will recognize or be able to ascertain using no more than routine experimentation, many equivalents to the specific embodiments of the invention described specifically herein. Such equivalents are intended to be encompassed in the scope of the claims.

What is claimed is:

1. A method of identifying a drug that inhibits the HIV membrane fusion machinery by inhibiting interactions between the N36 peptide trimer and the C34 peptide trimer of HIV gp41, comprising:

(a) combining HIV gp41 N36 peptide trimer, HIV gp41 C34 peptide trimer and a drug to be assessed for its ability to inhibit interaction between the two trimers, to produce a combination;

(b) maintaining the combination under conditions appropriate for interactions to occur between N36 peptide trimers and C34 peptide trimers; and (c) assessing whether interactions occurred between N36 peptide trimers and C34 peptide trimers, wherein if interactions between the N36 peptide trimer and the C34 peptide trimer did not occur in the presence of the drug or occurred to a lesser extent in the presence of the drug than in its absence, the drug is a drug that inhibits the HIV membrane fusion machinery.

2. The method of claim 1 wherein in step (c) the interaction assessed is packing of amino acid residues or peptides of C34 peptide trimers into highly conserved cavities on N36 peptide trimers.

3. The method of claim 2 wherein the interaction assessed is packing of amino acid residues or peptides of C34 into cavities on N36 peptide trimers which are:

(a) lined by Leu-566 of the left N36 helix and Leu-565 of the right N36 helix;

(b) formed on the left side by sidechains from the left N36 helix, including residues (top to bottom) Val-570, Lys-574 (aliphatic portion) and Gln-577;

(c) formed on the right side by residues Leu-568, Trp-571 and Gly-572 of the right N36 helix; and, (d) composed on its floor of Thr-569, Ile-573 and Leu-576 wherein amino acid numbers refer to the positions as indicated in FIG. 1.

4. A method of screening a library of compounds to identify compounds that inhibit the HIV membrane fusion machinery by inhibiting interaction between the N36 peptide trimer and the C34 peptide trimer of HIV gp41, comprising:

(a) combining HIV gp41 N36 peptide trimer, HIV gp41 C34 peptide trimer and at least one compound to be assessed for its ability to inhibit interaction between the two trimers, to produce a combination;

(b) maintaining the combination under conditions appropriate for interaction to occur between N36 peptide trimers and C34 peptide trimers;

(c) assessing whether interaction occurred between N36 peptide trimers and C34 peptide trimers; and (d) repeating steps (a), (b) and (c) for the remainder of the compounds of the library, wherein if interaction between the N36 peptide trimer and the C34 peptide trimer did not occur in the presence of the compound or occurred to a lesser extent in the presence of the compound than in its absence, the compound is a compound that inhibits the HIV membrane fusion machinery and the library has been screened to identify those compounds that inhibit the HIV membrane fusion machinery by inhibiting interaction between the N36 peptide trimer and the C34 peptide trimer of HIV gp41 compounds.

5. The method of claim 4, wherein in step (c) the interaction assessed is packing of amino acid residues or peptides of C34 peptide trimers into highly conserved cavities on N36 peptide trimers.

6. The method of claim 5, wherein the interaction assessed is packing of amino acid residues or peptides of C34 into cavities on N36 peptide trimers which are:

(a) lined by Leu-566 of the left N36 helix and Leu-565 of the right N36 helix;

(b) formed on the left side by sidechains from the left N36 helix, including residues (top to bottom) Val-570, Lys-574 (aliphatic portion) and Gln-577;

(c) formed on the right side by residues Leu-568, Trp-571 and Gly-572 of the right N36 helix; and (d) composed on its floor of Thr-569, Ile-573 and Leu-576, wherein amino acid numbers refer to the positions as indicated in FIG. 1.

* * * * *

SEQUENCE LISTING

<160> NUMBER OF SEQ ID NOS: 2

<210> SEQ ID NO 1
<211> LENGTH: 36
<212> TYPE: PRT
<213> ORGANISM: Human Immunodeficiency Virus

<400> SEQUENCE: 1

```
Ser Gly Ile Val Gln Gln Gln Asn Asn Leu Leu Arg Ala Ile Glu Ala
 1               5                  10                  15

Gln Gln His Leu Leu Gln Leu Thr Val Trp Gly Ile Lys Gln Leu Gln
            20                  25                  30
```

```
Ala Arg Ile Leu
        35

<210> SEQ ID NO 2
<211> LENGTH: 34
<212> TYPE: PRT
<213> ORGANISM: Human Immunodeficiency Virus

<400> SEQUENCE: 2

Trp Met Glu Trp Asp Arg Glu Ile Asn Asn Tyr Thr Ser Leu Ile His
1               5                   10                  15

Ser Leu Ile Glu Glu Ser Gln Asn Gln Gln Glu Lys Asn Glu Gln Glu
            20                  25                  30

Leu Leu
```